(12) United States Patent
Seow et al.

(10) Patent No.: US 11,826,114 B2
(45) Date of Patent: Nov. 28, 2023

(54) ROBOTIC SURGICAL SYSTEMS, INSTRUMENT DRIVE ASSEMBLIES, AND DRIVE ASSEMBLIES

(71) Applicant: Covidien LP, Mansfield, MA (US)

(72) Inventors: Chi Min Seow, New Haven, CT (US); Jaimeen Kapadia, Cambridge, MA (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 643 days.

(21) Appl. No.: 16/757,962

(22) PCT Filed: Nov. 20, 2018

(86) PCT No.: PCT/US2018/061916
§ 371 (c)(1),
(2) Date: Apr. 21, 2020

(87) PCT Pub. No.: WO2019/108437
PCT Pub. Date: Jun. 6, 2019

(65) Prior Publication Data
US 2020/0337788 A1    Oct. 29, 2020

Related U.S. Application Data

(60) Provisional application No. 62/592,382, filed on Nov. 29, 2017.

(51) Int. Cl.
*A61B 34/30* (2016.01)
*A61B 17/00* (2006.01)
(Continued)

(52) U.S. Cl.
CPC .............. *A61B 34/30* (2016.02); *A61B 17/29* (2013.01); *A61B 34/35* (2016.02);
(Continued)

(58) Field of Classification Search
CPC ......... A61B 34/30; A61B 17/29; A61B 34/35; A61B 2017/00367; A61B 2017/00398;
(Continued)

(56) References Cited

U.S. PATENT DOCUMENTS 4,281,447 A    8/1981 Miller et al.
4,993,132 A    2/1991 Manz
(Continued)

FOREIGN PATENT DOCUMENTS

EP    1570789 A2 *  9/2005 ............. A61B 17/29
KR    101633618 B1    6/2016
(Continued)

OTHER PUBLICATIONS

International Search Report dated Jan. 28, 2015 corresponding to counterpart Int'l Patent Application PCT/US2014/061329.
(Continued)

*Primary Examiner* — Joseph M Dietrich
*Assistant Examiner* — Michael T. Holtzclaw
(74) *Attorney, Agent, or Firm* — Carter, DeLuca & Farrell LLP

(57) ABSTRACT

A drive assembly of an instrument drive assembly, is provided. The drive assembly includes a drive screw, a drive nut, a follower, a biasing element, and a drive element. The drive nut is threadedly engaged with a threaded portion of the drive screw such that rotation of the drive screw results in longitudinal movement of the drive nut. The follower is longitudinally slidable with respect to the drive screw. The biasing element is disposed in mechanical cooperation with the drive nut and the follower. The drive element is disposed in mechanical cooperation with the follower. Longitudinal translation of the drive element is configured to drive a function of the surgical instrument.

10 Claims, 25 Drawing Sheets

(51) Int. Cl.
*A61B 17/29* (2006.01)
*A61B 34/35* (2016.01)
(52) U.S. Cl.
CPC ............... *A61B 2017/00367* (2013.01); *A61B 2017/00398* (2013.01); *A61B 2017/00477* (2013.01); *A61B 2017/2946* (2013.01)
(58) Field of Classification Search
CPC .. A61B 2017/00477; A61B 2017/2946; A61B 34/37
See application file for complete search history.

(56) References Cited

U.S. PATENT DOCUMENTS

| | | |
|---|---|---|
| 5,820,623 A | 10/1998 | Ng |
| 6,436,107 B1 | 8/2002 | Wang et al. |
| 6,969,385 B2 | 11/2005 | Moreyra |
| 7,762,825 B2 | 7/2010 | Burbank et al. |
| 7,963,913 B2 | 6/2011 | Devengenzo et al. |
| 8,573,465 B2 | 11/2013 | Shelton, IV |
| 8,601,667 B2 | 12/2013 | Norton |
| 8,602,031 B2 | 12/2013 | Reis et al. |
| 8,758,352 B2 | 6/2014 | Cooper et al. |
| 11,058,508 B2 * | 7/2021 | Scheib .................... A61B 17/00 |
| 2006/0074415 A1 | 4/2006 | Scott et al. |
| 2007/0142971 A1 | 6/2007 | Schena |
| 2008/0108443 A1 | 5/2008 | Jinno et al. |
| 2008/0140088 A1 | 6/2008 | Orban, III |
| 2011/0213384 A1 | 9/2011 | Jeong |
| 2011/0282358 A1 | 11/2011 | Gomez et al. |
| 2011/0301637 A1 | 12/2011 | Kerr et al. |
| 2012/0116416 A1 | 5/2012 | Neff et al. |
| 2012/0158013 A1 | 6/2012 | Stefanchik et al. |
| 2013/0110131 A1 | 5/2013 | Madhani et al. |
| 2013/0325034 A1 | 12/2013 | Schena et al. |
| 2014/0000411 A1 | 1/2014 | Shelton, IV et al. |
| 2014/0166023 A1 | 6/2014 | Kishi |
| 2014/0180309 A1 | 6/2014 | Seeber et al. |
| 2016/0199138 A1 | 7/2016 | Cooper et al. |
| 2016/0206310 A1 * | 7/2016 | Shelton, IV ..... A61B 17/07207 |
| 2017/0065365 A1 * | 3/2017 | Schuh .................... A61B 90/50 |
| 2017/0119421 A1 | 5/2017 | Staunton et al. |
| 2020/0375585 A1 * | 12/2020 | Swayze ................ A61B 17/29 |

FOREIGN PATENT DOCUMENTS

| | | |
|---|---|---|
| WO | 2011037394 A2 | 3/2011 |
| WO | WO-2014134034 A2 * | 9/2014 .......... A61B 17/068 |
| WO | 2015023834 A1 | 2/2015 |
| WO | 2015088647 A1 | 6/2015 |
| WO | 2017120028 A1 | 7/2017 |

OTHER PUBLICATIONS

Partial Supplementary European Search Report dated Jul. 16, 2021 corresponding to counterpart Patent Application EP 18882357.9.
Extended European Search Report dated Nov. 22, 2021 corresponding to counterpart Patent Application EP 18882357.9.

* cited by examiner

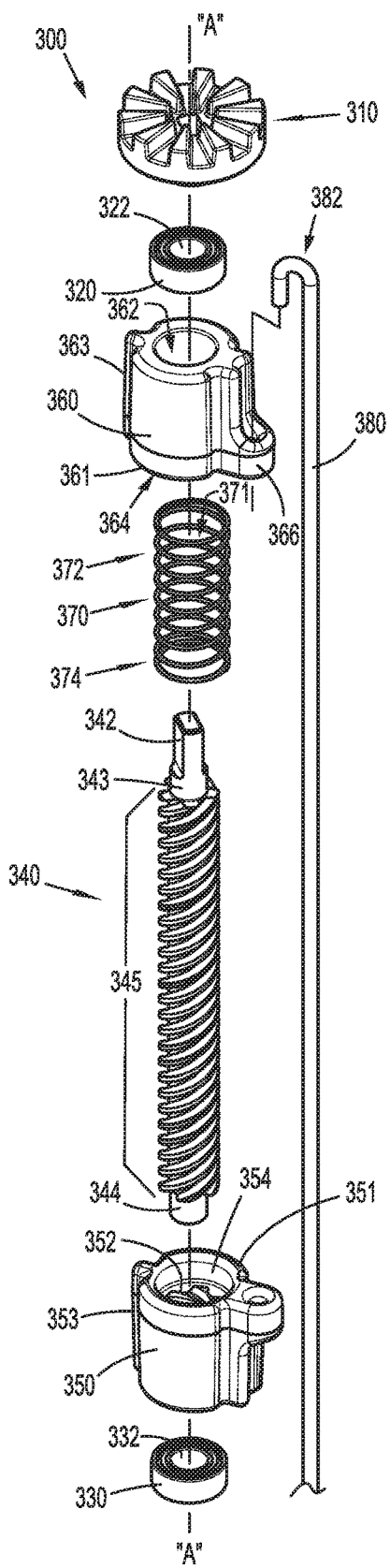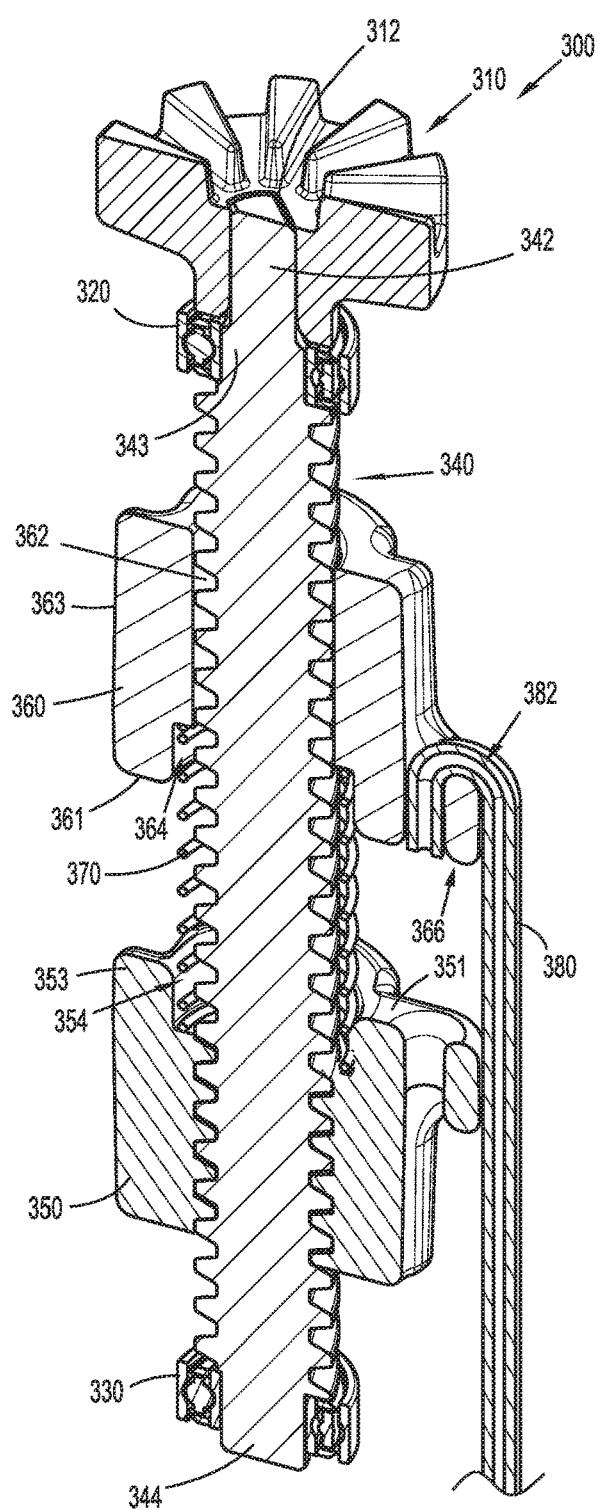
FIG. 8
FIG. 9

ROBOTIC SURGICAL SYSTEMS, INSTRUMENT DRIVE ASSEMBLIES, AND DRIVE ASSEMBLIES

CROSS-REFERENCE TO RELATED APPLICATIONS

This application is a U.S. National Stage Application filed under 35 U.S.C. § 371(a) of International Patent Application Serial No. PCT/US2018/061916, filed Nov. 20, 2018, which claims the benefit of and priority to U.S. Provisional Patent Application Ser. No. 62/592,382, filed Nov. 29, 2017, the entire disclosure of which is incorporated by reference herein.

BACKGROUND

Robotic surgical systems have been used in minimally invasive medical procedures. Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

Cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the wrist assembly and/or the end effector.

In some instances, the wrist assembly provides three degrees of freedom for movement of the end effector through the use of cables or cable pairs, one for each degree of freedom. For example, for grasping or cutting end effectors, the wrist assembly provides the three degrees of freedom by allowing changes to a pitch, a yaw, and an opening and closing of the end effector.

Prior to or during use of the robotic system, surgical instruments are selected and connected to instrument drive assemblies of each robot arm. For proper installation to be completed, certain connecting features of the surgical instrument must be matingly engaged to corresponding connecting features of the instrument drive assembly. Once these features are matingly engaged, the instrument drive assembly can drive the actuation of the surgical instrument.

Accordingly, there is a need for instrument drive assemblies that are robust, secure, and that can efficiently drive actuation of the surgical instrument.

SUMMARY

The present disclosure relates to an interface for use with a surgical system. The interface includes a proximal body portion, a distal body portion, a cavity, a proximal coupler, a distal coupler, and a biasing element. The proximal body portion is configured to mechanically engage an instrument control unit of the surgical system. The distal body portion is disposed in mechanical cooperation with the proximal body portion and is configured to mechanically engage an instrument drive assembly of the surgical system. The cavity is defined between the proximal body portion and the distal body portion. The proximal coupler is disposed at least partially within the cavity and is configured to engage a driving element of the instrument control unit. The distal coupler is disposed at least partially within the cavity and is configured to engage a driven element of the instrument drive assembly. The biasing element is disposed in mechanical cooperation with at least one of the proximal coupler and the distal coupler.

In disclosed embodiments, the biasing element is configured to bias the proximal coupler proximally. Additionally, the biasing element may be configured to bias the distal coupler distally.

It is further disclosed that the biasing element includes a compression spring.

In embodiments, the biasing element includes at least one magnet. The biasing element may include a first magnet disposed in mechanical cooperation with the proximal coupler and a second magnet disposed in mechanically cooperation with the distal coupler.

It is also disclosed that the proximal coupler and the distal coupler are coaxial.

In disclosed embodiments, the interface includes a second proximal coupler disposed at least partially within the cavity and configured to mechanically engage an instrument drive assembly of the surgical system, and a second distal coupler disposed at least partially within the cavity and configured to mechanically engage a driven element of the surgical system. The second proximal coupler and the second distal coupler may be coaxial.

It is further disclosed that the proximal coupler includes a plurality of legs and the distal coupler includes a plurality of legs. Each leg of the plurality of legs of the proximal coupler is positioned adjacent two legs of the plurality of legs of the distal coupler. Additionally, each leg of the plurality of legs of the proximal coupler may be positioned between and in contact with two legs of the plurality of legs of the distal coupler.

The present disclosure also relates to an instrument drive assembly for use with a surgical instrument. The instrument drive assembly includes a proximal housing, a distal housing, and a locking mechanism configured to facilitate engagement between the proximal housing and the distal housing. The locking mechanism includes a locking collar, a flexure ring, and a cup. The locking collar is disposed in mechanical cooperation with the proximal housing. The flexure ring is disposed in mechanical cooperation with the proximal housing. The cup is disposed in mechanical cooperation with the distal housing. The locking collar is longitudinally translatable with respect to the proximal housing from a proximal position to a distal position. At least one finger of the flexure ring is configured to engage a lip of the cup to secure the proximal housing to the distal housing when the locking collar is in the distal position.

In disclosed embodiments, the locking collar is biased distally.

It is further disclosed that a tapered portion of the flexure ring is configured to engage a tapered portion of the cup to limit distal movement of the proximal housing with respect to the distal housing.

In embodiments of the present disclosure, the locking mechanism includes a locking ring disposed in mechanical cooperation with the proximal housing. A plurality of protrusions of the locking ring may be configured to engage the cup to limit rotational movement of the proximal housing with respect to the distal housing.

Additionally, the present disclosure includes a wire channel disposed on an exterior surface of the proximal housing that is configured to removably receive a wire at least partially therein.

In disclosed embodiments, the instrument drive assembly includes a motor disposed at least partially within the proximal housing, and a compliant member disposed in contact with a distal portion of the motor. The compliant member may include at least one of silicone, fluoroelastomer, rubber, ethylene propylene diene terpolymer ("EPDM"), and nitrile rubber.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 8 is an exploded view of the drive assembly of FIGS. 5-7;

FIG. 9 is a perspective, cross-sectional view of the drive assembly of FIGS. 5-8, as taken along line 9-9 of FIG. 5;

DETAILED DESCRIPTION

Figure 1B:
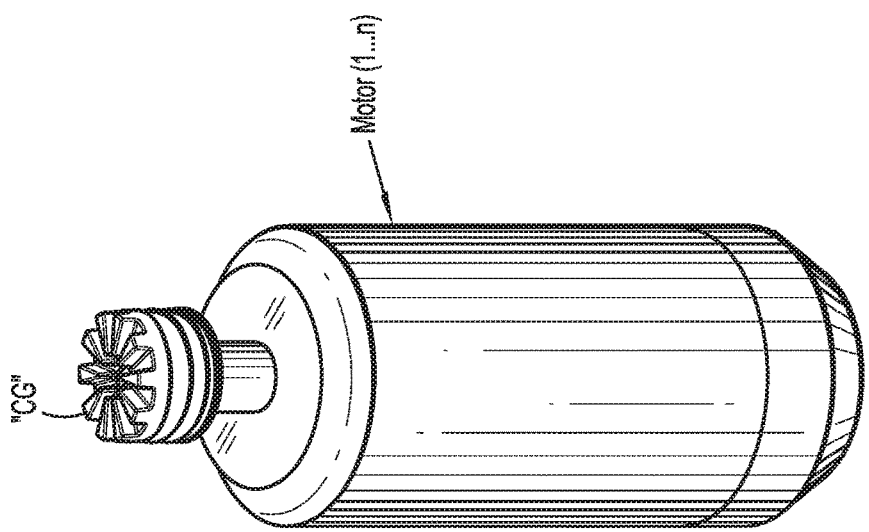
FIG. 1B is a schematic, perspective view of a motor of a control device of the medical work station of FIG. 1A.

Embodiments of the presently disclosed instrument drive assemblies are described in detail with reference to the drawings, in which like reference numerals designate identical or corresponding elements in each of the several views. As used herein the term "distal" refers to that portion of the instrument drive assembly that is farther from the user, while the term "proximal" refers to that portion of the instrument drive assembly that is closer to the user.

Figure 1A:
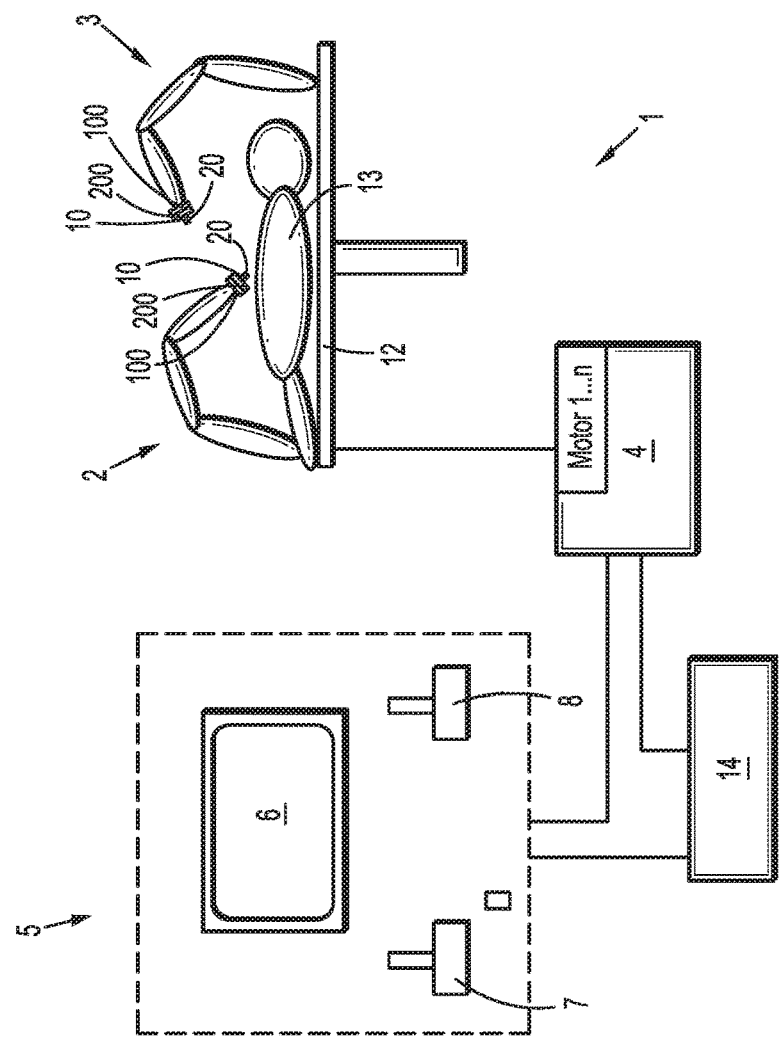
FIG. 1A is a schematic illustration of a medical work station and operating console in accordance with the present disclosure.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an instrument control unit 100, to which may be attached, for example, a surgical instrument 10 having an instrument drive assembly 200, and supporting an end effector 20 having jaw members 22 and 24, in accordance with the embodiments of instrument drive assemblies 200 disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument control units 100, and thus the surgical instruments 10 execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of surgical instrument 10. Medical work station 1 may also include more than two robot arms 2, 3, the additional robot arms likewise being connected to control device 4 and being telemanipulatable by means of operating console 5. An instrument control unit and a surgical instrument may also be attached to the additional robot arm. Medical work station 1 may include a database 14, in particular coupled to with control device 4, in which are stored for example pre-operative data from patient 13 and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (e.g., "M1"-"M6"). Motors may be part of instrument control unit 100 and/or disposed externally of instrument control unit 100. Motors "M" (e.g., motors "M" being located externally of instrument control unit 100) may be configured to rotate a crown gear "CG" (FIG. 1B), or the like, that is keyed to or non-rotatably supported on a rotatable shaft of at least some of motors "M." In use, as motors "M" are driven, the rotation of crown gear(s) "CG" effects operation and/or movement of instrument drive assembly 200 of surgical instrument 10, as discussed below. It is further envisioned that at least one motor "M" receives signals wirelessly (e.g., from control device 4). It is contemplated that control device 4 coordinates the activation of the various motors (Motor 1 . . . n) to coordinate an operation and/or movement of surgical instrument 10. It is envisioned that each motor corresponds to a separate degree of freedom of surgical instrument 10 engaged with instrument control unit 100. It is further envisioned that more than one motor, including every motor (Motor 1 . . . n), is used for each degree of freedom. Reference may be made to commonly owned International Patent Application No. PCT/US14/61329, filed on Oct. 20, 2014 entitled "Wrist and Jaw Assemblies for Robotic Surgical Systems," the entire content of which is incorporated herein by reference, for a detailed discussion of illustrative examples of the construction and operation of end effectors 20 for use with instrument control unit 100.

Turning now to FIGS. 1C-13, instrument drive assembly 200 is shown having surgical instrument 10 extending distally therefrom, and which is configured to engage instrument control unit 100, as described above. Instrument drive assembly 200 is configured to transfer rotational movement supplied by instrument control unit 100 (e.g., via motors "M") into longitudinal movement of drive members 380 to effect various functions of end effector 20.

With reference to FIGS. 1C, and 2-5, instrument drive assembly 200 includes a housing assembly 205 which includes a proximal housing 210 and a distal housing 220. Proximal housing 210 and distal housing 220 are releasably coupled to each other, which may facilitate assembly of instrument drive assembly 200, and which may facilitate access, repair, and/or replacement of parts housed at least partially therein. Housing assembly 205 defines at least one bore 207 for housing drive assemblies 300. It is envisioned that housing assembly 205 includes four separate bores 207, where each bore 207 is at least partially separated from each other and where each bore 207 is configured to house a single drive assembly 300. Additionally, as discussed below, bore 207 includes longitudinally-extending channels 206 (e.g., four channels 206) therein. Each channel 206 is configured to slidingly accept a rail 353 of drive nut 350 and a rail 363 of follower 360. It is further envisioned that each bore 207 includes two separate channels 206, where one channel 206 is configured to slidingly accept rail 353 of drive nut 350 and where the other channel 206 is configured to slidingly accept rail 363 of follower 360

Figure 2:
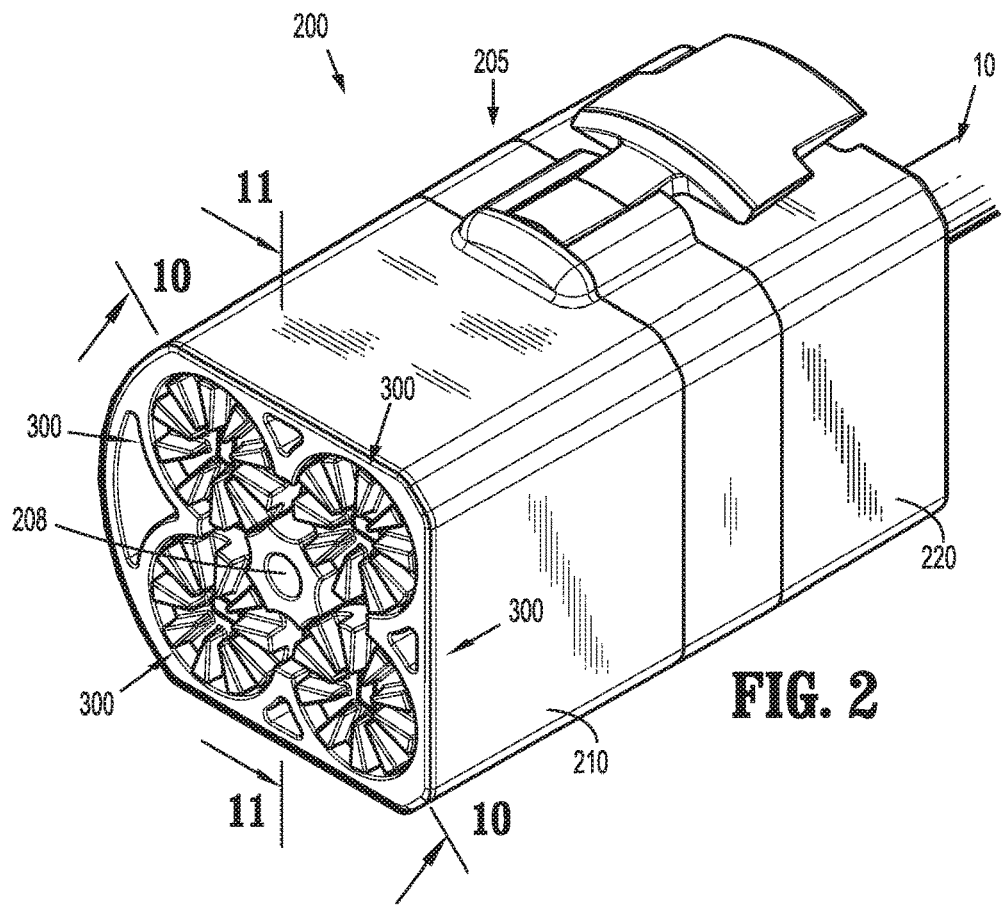
FIG. 2 is an enlarged view of the area of detail indicated in FIG. 1C.
Figure 3:
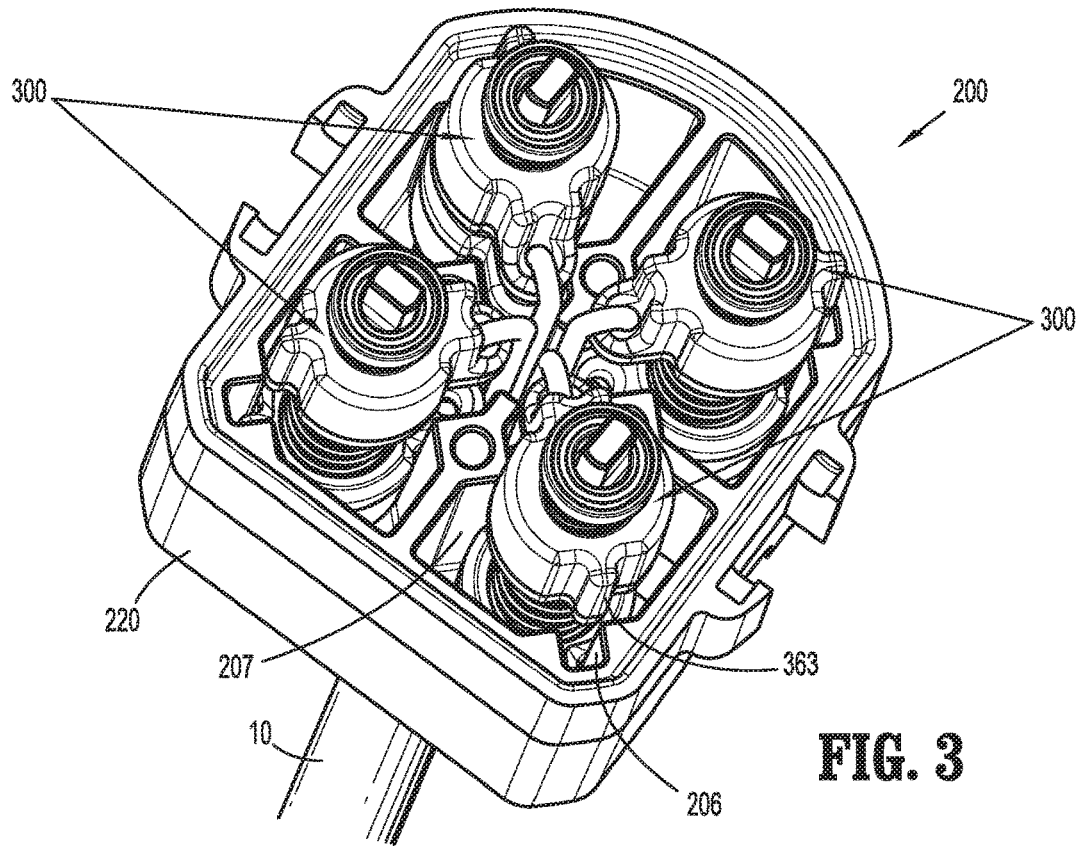
FIG. 3 is a distally-facing perspective view of a portion of the instrument drive assembly of FIGS. 1C and 2 with various parts removed therefrom.
Figure 4:
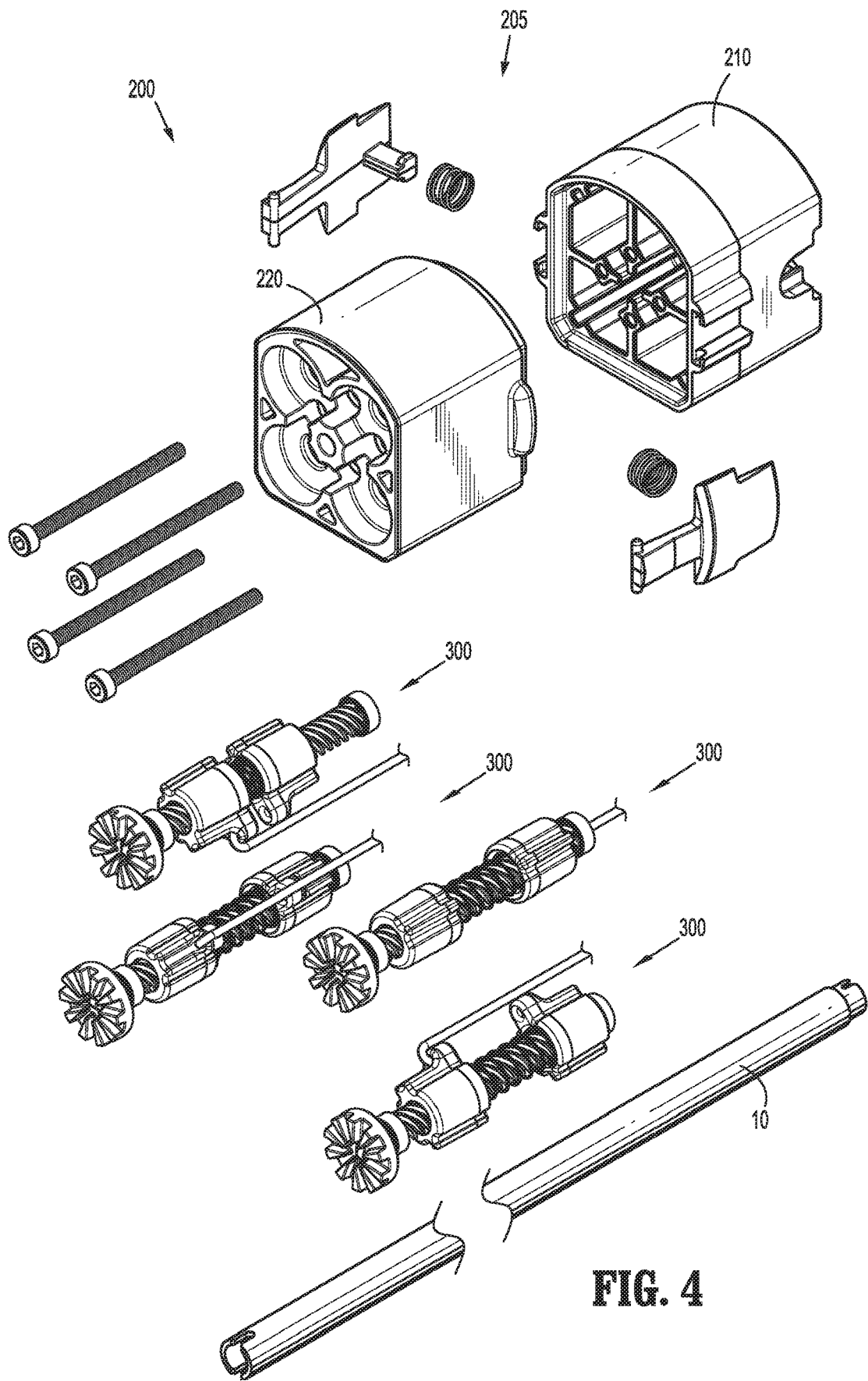
FIG. 4 is an exploded view of the instrument drive assembly of FIGS. 1C-3.

With continued reference to FIGS. 2-4, instrument drive assembly 200 also includes a plurality of drive assemblies 300. In the illustrated embodiment, instrument drive assembly 200 includes four drive assemblies 300, however instrument drive assembly 200 may include more (e.g., five or six) or fewer (e.g., three) drive assemblies 300 without departing from the scope of the present disclosure.

With reference to FIGS. 5-9, each drive assembly 300 includes a proximal gear 310, a proximal bearing 320, a distal bearing 330, a drive screw 340, a drive nut 350, a follower 360, a biasing element 370, and drive member (e.g., a flexible cable) 380. Proximal gear 310 is configured to engage with an instrument control gear (e.g., crown gear "CG" of motor "M") of instrument control unit 100, such that rotation of crown gear "CG" causes a corresponding rotation of proximal gear 310. Proximal gear 310 may be a crown gear "CG" that is configured to mate with and/or mesh with crown gear "CG" of motor "M," or with a distal portion 651 of a coupler 650 of an interface 600 (FIGS. 22-26) which mate with and/or engage with crown gear "CG" of motor "M."

With particular reference to FIGS. 8 and 9, proximal gear 310 includes an aperture 312 extending longitudinally therethrough, which is configured to mechanically engage a proximal portion 342 of drive screw 340. As shown, aperture 312 and proximal portion 342 of drive screw 340 have corresponding, non-circular cross-sections, such that proximal gear 310 and drive screw 340 are keyed to one another, which results in a rotationally fixed connection therebetween. Accordingly, rotation of proximal gear 310 results in a corresponding rotation of drive screw 340.

Figure 10:
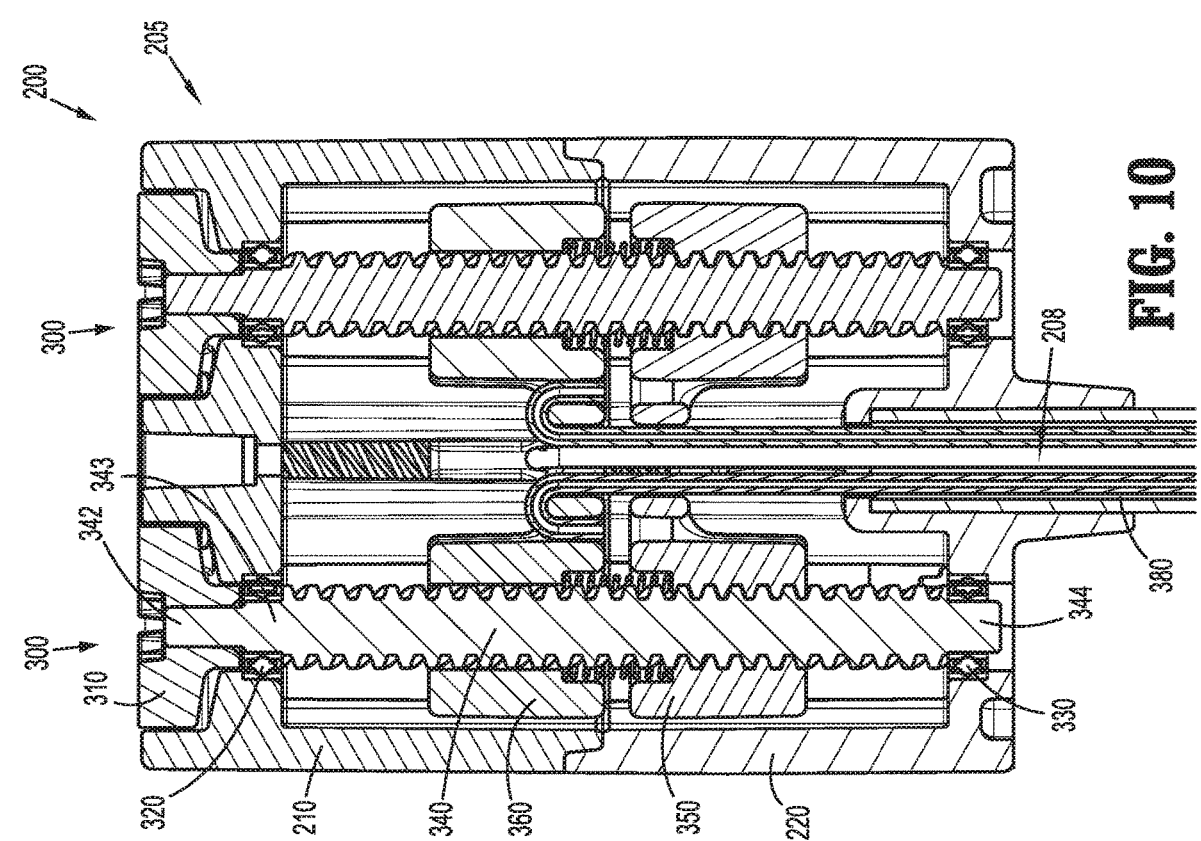
FIG. 10 is a cross-sectional view of the instrument drive assembly of the present disclosure taken along line 10-10 of FIG. 2.
Figure 13:
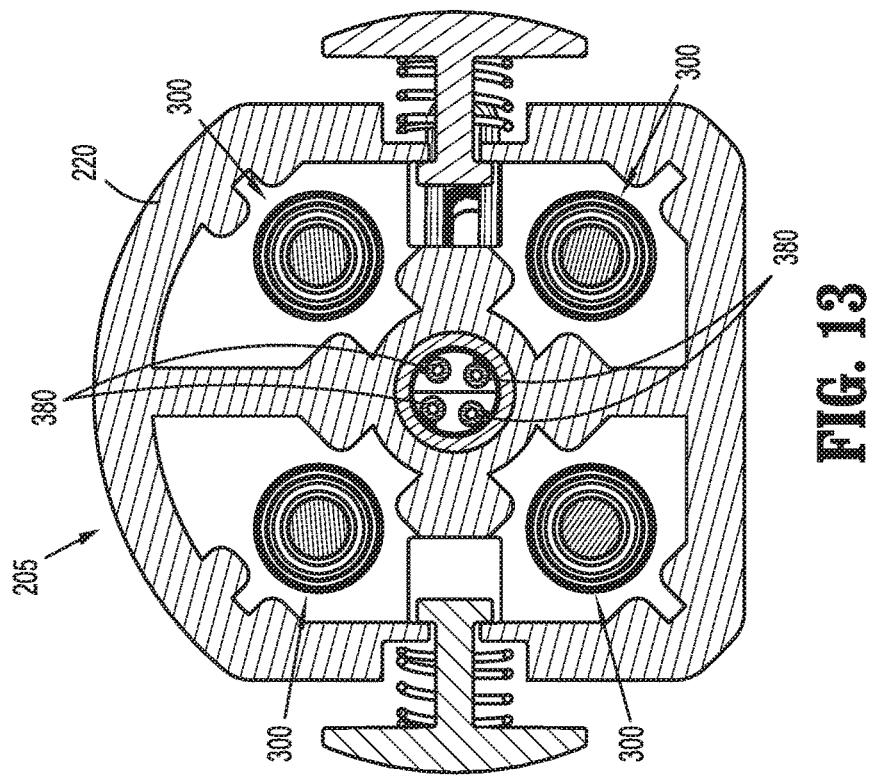
FIG. 13 is a transverse cross-sectional view of the instrument drive assembly of the present disclosure taken along line 13-13 of FIG. 11.
Figure 12:
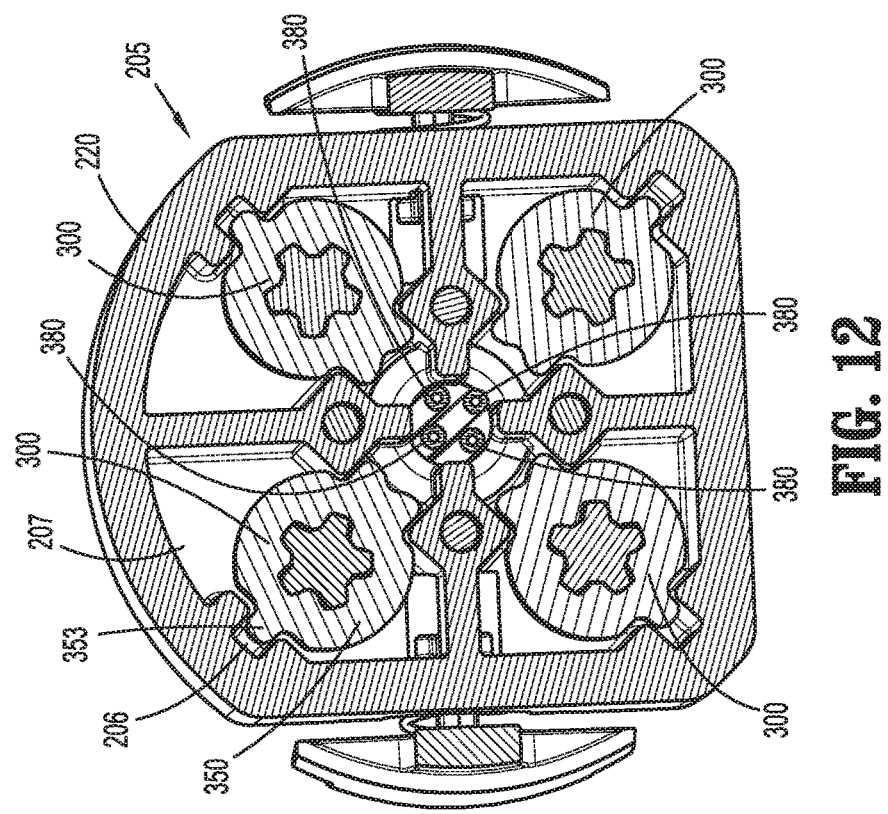
FIG. 12 is a transverse cross-sectional view of the instrument drive assembly of the present disclosure taken along line 12-12 of FIG. 11.

Proximal bearing 320 is disposed about a proximal shaft 343 of drive screw 340 adjacent a portion of proximal housing 210, and distal bearing 330 is disposed about a distal shaft 344 of drive screw 340 adjacent a portion of distal housing 220 (see FIG. 10, for example). Each of proximal bearing 320 and distal bearing 330 permits or facilitates rotation of drive screw 340 with respect to housing assembly 205. Additionally, proximal bearing 320 may be configured to function as a proximal stop for follower 360, and distal bearing 330 may be configured to function as a distal stop for drive nut 350.

Drive screw 340 includes a proximal portion 342, a proximal shaft 343, a distal shaft 344 and a threaded portion 345, and defines a longitudinal axis "A-A" extending through a radial center thereof (see FIG. 8). Rotation of proximal gear 310 causes drive screw 340 to rotate about longitudinal axis "A-A" in a corresponding direction and rate of rotation.

Drive nut 350 includes a threaded aperture 352 extending longitudinally therethrough, which is configured to mechanically engage threaded portion 345 of drive screw 340. Drive nut 350 is configured to be positioned on drive screw 340 in a manner such that rotation of drive screw 340 causes longitudinal movement of drive nut 350. That is, drive nut 350 and drive screw 340 are threadedly engaged with each other. Moreover, rotation of proximal gear 310 in a first direction (e.g., clockwise) causes drive nut 350 to move in a first longitudinal direction (e.g., proximally) with respect to proximal portion 342 of drive screw 340, and rotation of proximal gear in a second direction (e.g., counterclockwise) causes drive nut 350 to move in a second longitudinal direction (e.g., distally) with respect to proximal portion 342 of drive screw 340. Drive nut 350 also includes a retention pocket 354 disposed proximally adjacent threaded aperture 352. Retention pocket 354 includes a larger inner diameter than threaded aperture 352, and is configured to house at least a portion of biasing element 370, as discussed in further detail below.

Drive nut 350 includes a rail 353 extending longitudinally along an outer surface thereof, and which is configured to be slidably disposed in a longitudinally extending channel 206 formed in bore 207 of housing assembly 205 (see FIGS. 5-7 and 12, for example). Rail 353 of drive nut 350 cooperates with channel 206 of bore 207 of housing assembly 205 to inhibit or prevent drive nut 350 from rotating about longitudinal axis "A-A" as drive screw 340 is rotated.

Follower 360 includes a rail 363 extending longitudinally along an outer surface thereof, and which is configured to be slidably disposed in longitudinal extending channel 206 formed in bore 207 of housing assembly 205 (see FIGS. 3, 5-7 and 12, for example). Rail 363 of follower 360 cooperates with channel 206 of bore 207 of housing assembly 205 to inhibit or prevent follower 360 from rotating about longitudinal axis "A-A" as drive screw 340 is rotated.

Follower 360 includes a non-threaded aperture 362 extending longitudinally therethrough, which is configured to slidingly engage threaded portion 345 of drive screw 340. That is, follower 360 is non-threadedly engaged with and slidably supported on drive screw 340. It is also disclosed that follower 360 does not engage drive screw 340, and that follower 360 is solely guided by the geometry (e.g., channel 206) of housing assembly 205. Follower 360 includes a retention pocket 364 disposed distally adjacent aperture 362. Retention pocket 364 includes a larger inner diameter than aperture 362, and is configured to house at least a portion of biasing element 370, as discussed in further detail below. Follower 360 also includes an engagement portion 366 disposed adjacent a radially outward surface thereof, which is configured to mechanically engage a proximal portion 382 of drive member 380.

In the illustrated embodiment, follower 360 is disposed proximally of drive nut 350, but the present disclosure also includes embodiments where follower 360 is disposed distally of drive nut 350. In such embodiments, retention pocket 354 of drive nut 350 would be disposed at a distal location thereof, and retention pocket 364 of follower 360 would be disposed at a proximal location thereof. Here, it is envisioned that follower 360 pulls drive member 380 distally, rather than follower 360 pushing drive member 380 proximally.

Biasing element 370, e.g., a compression spring, is configured to radially surround a portion of threaded portion 345 of drive screw 340. That is, drive screw 340 extends through an aperture 371 defined by and extending longitudinally through biasing element 370. Additionally, as seen in FIG. 9, a proximal portion 372 of biasing element 370 is configured for reception at least partially within retention pocket 364 of follower 360, and a distal portion 374 of biasing element 370 is configured for reception at least partially within retention pocket 354 of drive nut 350. In disclosed embodiments, proximal portion 372 of biasing element 370 is immovably fixed to follower 360, and distal portion 374 of biasing element 370 is immovably fixed to drive nut 350. It is envisioned that a compressed length of biasing element 370 is equal to or slightly smaller than a combined longitudinal length of retention pocket 364 of follower 360 and retention pocket 354 of drive nut 350, thus allowing contact between a proximal face 351 of drive nut 350 and a distal face 361 of follower 360 (see FIG. 6). While the illustrated embodiments show a particular type of biasing element 370 (i.e., a compression spring), other types of biasing elements are contemplated by the present disclosure.

Drive member 380 extends distally from follower 360, through a central bore 208 (FIGS. 2 and 10) of housing assembly 205, and is configured to mechanically engage a portion of surgical instrument 10, e.g., end effector 20. More particularly, each drive assembly 300 is oriented within housing assembly 205 such that the drive member 380 of each drive assembly 300 is centrally located within housing assembly 205 (see FIGS. 10-13), and extends through an elongated portion of surgical instrument 10 and into engagement with end effector 20, for example. It is envisioned that the surgical instrument 10 includes projections or the like to help guide or route drive members 380 between the drive assembly 300 and the end effector, for example.

Longitudinal translation of drive member 380 is configured to drive a function of end effector 20. For example, distal translation of a particular drive member 380 may be configured to approximate jaw members 22 and/or 24 with respect to the other, and proximal translation of drive member 380 may be configured to move at least one jaw member 22 away from the other jaw member 24, for instance. Additionally, distal translation of a drive member 380 of a different drive assembly 300 of instrument drive assembly 200 may be configured to articulate jaw members 22, 24 in a first direction, and proximal translation of the this drive member 380 may be configured to articulate jaw members 22, 24 in a second direction.

Additionally, since drive member 380 may be flexible and follow a particular path through surgical instrument 10, including a central portion of housing assembly 205, it may be beneficial to maintain drive member 380 in tension to prevent slack or to reduce the amount of slack in drive member 380. Without the benefit of the present disclosure, a user who manually (e.g., by hand) opens or otherwise manipulates jaw members to inspect and/or clean the jaw members, for example, may exert a proximal force on at least one drive member. That is, opening jaw members of a surgical instrument may cause at least a portion of at least one of its drive members to move proximally. In systems where drive members are directly connected to a drive nut, and where the drive nut is threadedly engaged with a drive screw, the engagement between the drive screw and the drive nut would prevent proximal translation of the drive nut in response to proximal translation of the drive member. Accordingly, proximal movement of the drive member (e.g., caused by manipulating the jaw members) may cause the drive member to go slack, and may cause the drive member to fall off of pulleys within the surgical instrument and/or become dislodged from retention pockets, for example. Instrument drive assembly 200 of the present disclosure prevents or minimizes the possibility of drive members 380 losing their tension and going slack.

During a use of instrument drive assembly 200 in the active state (i.e., when motor(s) "M" of instrument control unit 100 are used to rotate proximal gear(s) 310), rotation of proximal gear 310 results in a corresponding rotation of drive screw 340. Rotation of drive screw 340 causes longitudinal translation of drive nut 350 due to the engagement between threaded portion 345 of drive screw 340 and threaded aperture 352 of drive nut 350. As discussed above, the direction of longitudinal translation of drive nut 350 is determined by the direction of rotation of proximal gear 310, and thus drive screw 340. With particular reference to FIG.

6, which illustrates proximal face 351 of drive nut 350 abutted against distal face 361 of follower 360 (i.e., in the active state), proximal translation of drive screw 340 results in a corresponding proximal translation of follower 360, and thus a corresponding proximal translation of a respective drive member 380 which is engaged with follower 360.

Additionally, when one drive nut 350 moves in a first longitudinal direction (e.g., proximally), it is envisioned that a drive nut 350 from a different drive assembly 300 is forced to correspondingly move in a second, opposite longitudinal direction (e.g., distally). Such configurations function to compensate for any slack in drive members 380. Moreover, once all drive nuts 350 are engaged with respective followers 360 (e.g., compressing biasing element 370; see FIG. 6), and when the system is so-called "stiff" (i.e., no stretch in drive members 380), the sum of the displacements of the four drive members 380 must be zero. For example, if one drive member 380 moves distally two units, two other drive members 380 can move proximally one unit each, and the fourth drive member 380 would not move, thus preserving the net zero displacement.

This movement of drive nuts 350, followers 360 and drive members 380 is controlled by motors "M" and system controls. When a drive nut 350 moves distally without corresponding proximal movement of a drive member 380, the drive nut 350 would separate from follower 360 with that drive assembly 300 (see FIGS. 5 and 7). These features help achieve zero displacement by preventing slack in drive members 380.

Figure 7:
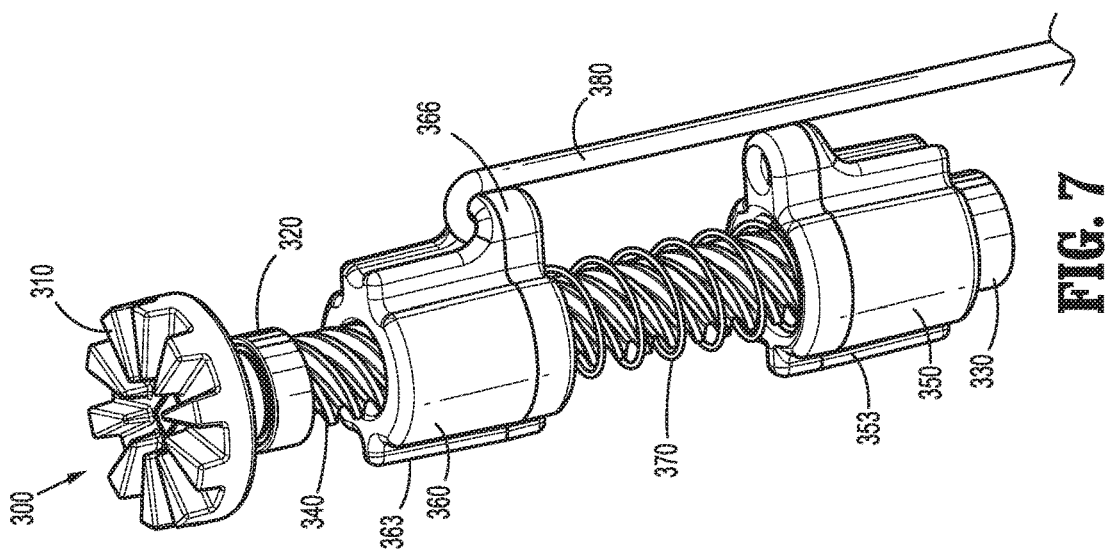
FIGS. 5-7 are perspective views of a drive assembly of the instrument drive assembly of FIGS. 1C-4 shown at various points of operation.
Figure 5:
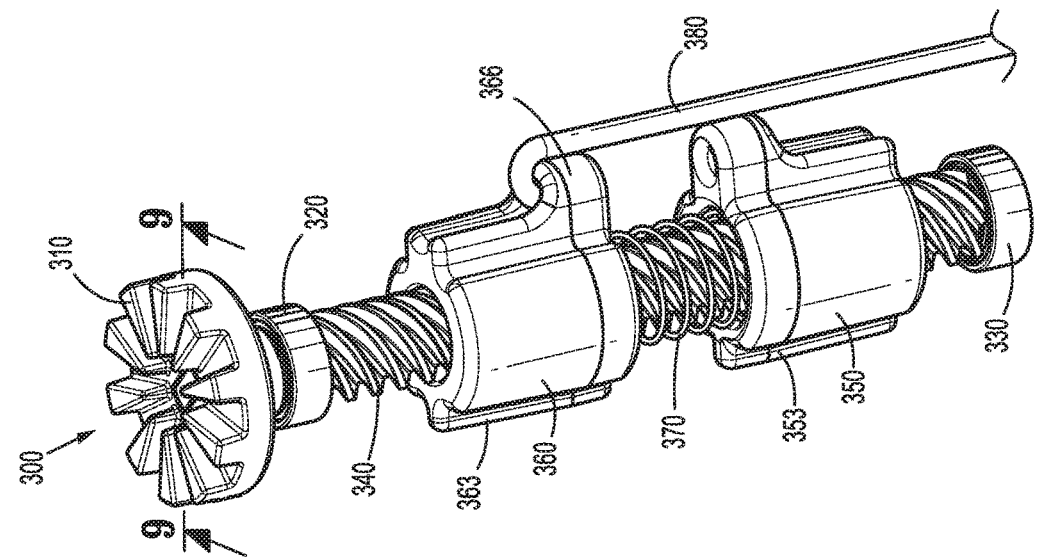
Figure 11:
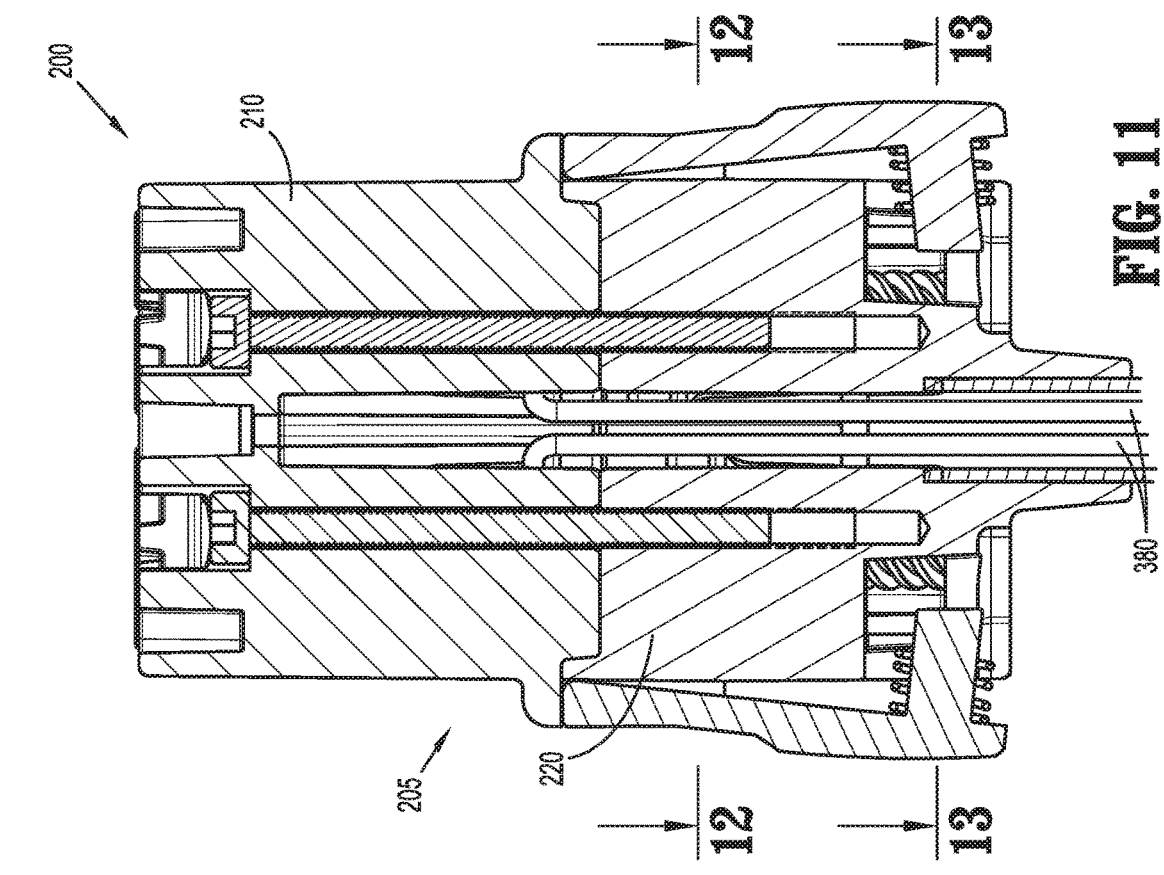
FIG. 11 is a cross-sectional view of the instrument drive assembly of the present disclosure taken along line 11-11 of FIG. 2.

More particularly, in FIGS. 5 and 7, drive nut 350 has separated from follower 360. Here, this drive assembly 300 may not be capable of effectively translating a meaningful load to drive member 380, but drive member 380 and follower 360 are capable of translating relatively freely (or unimpeded) proximally and distally. Such a configuration or ability is helpful to allow a wrist assembly to be externally manipulated separate from the system control. In FIG. 5, drive nut 350 has been driven proximally such that biasing element 370 has been partially compressed, in FIG. 7 biasing element 370 has been compressed less than in FIG. 5 (e.g., biasing element 370 has not been compressed).

Figure 6:
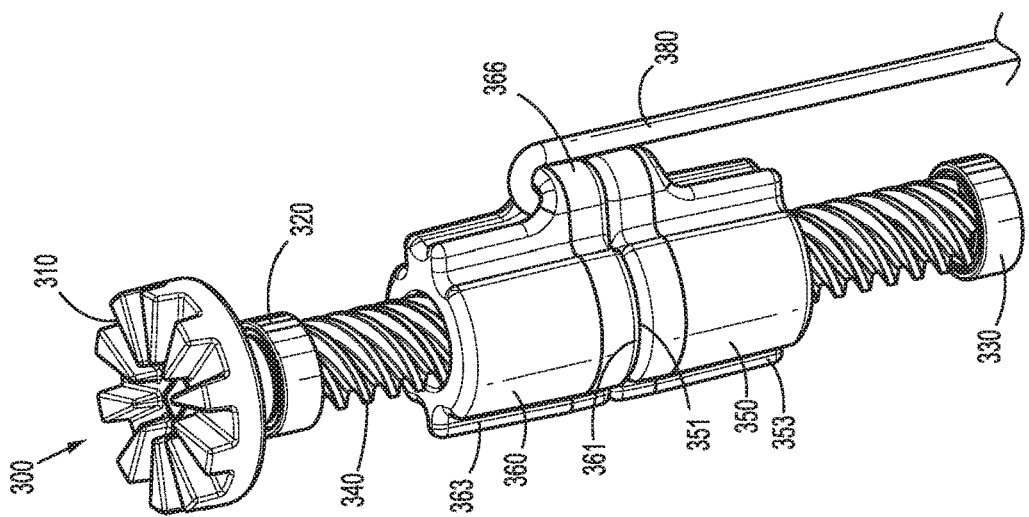

In FIG. 6, drive assembly 300 is in an "active use state" where drive nut 350 has been driven into contact with follower 360, and pre-tension has been added to drive member 380, for example. When each of the four drive assemblies 300 is in this position, the system is not back-drivable; an external force on the jaw members 22, 24 or wrist assembly would not result in movement of drive assemblies 300.

During use of instrument drive assembly 200 in the passive state (i.e., when jaw members 22, 24 are being manipulated manually), manual manipulation of jaw members 22, 24 results in longitudinal movement of follower 360 while maintaining some level of tension of drive member 380. More particularly, in disclosed embodiments, manipulation of jaw members 22, 24 (e.g., moving one jaw member 22 away from the other 24) causes proximal movement of one drive member 380. As described above, proximal movement of a drive member in a different instrument (not employing the principles of the present disclosure) may cause the drive member to lose its tension or stretch and thus cause undesirable effects. Here, however, proximal movement of the one drive member 380 results in a corresponding proximal movement of follower 360 because follower 360 is slidable with respect to drive screw 340 and is not threadedly engaged therewith. At least some level of tension in drive member 380 remains because of biasing element 370, which is engaged with both follower 360 and drive nut 350, which provides an opposite force against follower 360. That is, if the one drive member 380 is moved proximally, and thus exerts a proximal force on follower 360, this force is resisted and/or counter-balanced by biasing element 370, thus retaining tension in drive member 380. Likewise, if the one drive member 380 is moved distally and thus exerts a distal force on follower 360, this force is also resisted and/or counter-balanced by biasing element 370, thus retaining at least some level of tension in drive member 380.

The present disclosure includes a robotic surgical system having an instrument control unit 100 including four independently-controlled motors "M," and an instrument drive assembly 200, from which a surgical instrument 10 extends, including four drive assemblies 300, with each drive assembly 300 selectively connectable to a respective motor "M" of instrument control unit 100, for example, as described above. Additionally, the present disclosure includes methods of controlling a surgical instrument 10 of instrument drive assembly 200 including the use of instrument control unit 100, and methods of performing a surgical task using instrument control unit 100 and instrument drive assembly 200. The present disclosure further includes methods of manually manipulating jaw members 22, 24 while maintaining tension in drive members 380.

Figure 14:
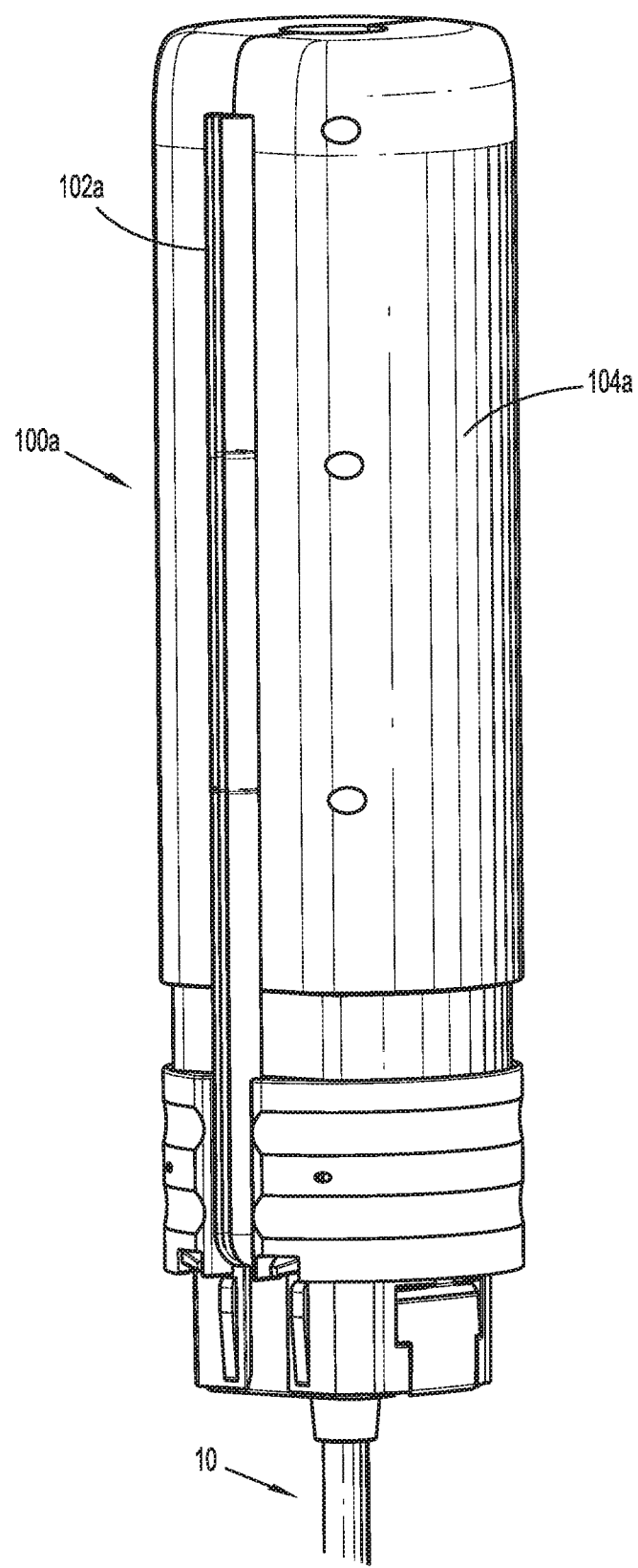
FIG. 14 is a perspective view of an instrument control unit in accordance with embodiments of the present disclosure.
Figure 15:
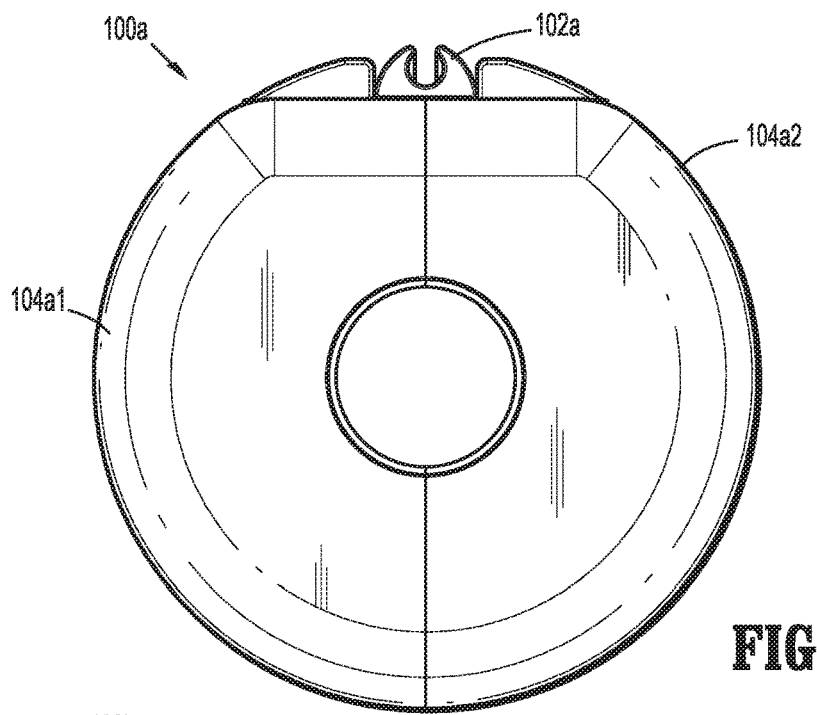
FIG. 15 is a top view of the instrument control unit of FIG. 14.

An additional embodiment of an instrument control unit is shown in FIGS. 14-15 and is indicated by reference character 100a. Instrument control unit 100a is designed for use with surgical instruments 10 including a wire (e.g., an electrical cord). Moreover, surgical instrument 10 may include monopolar curved scissors, a vessel sealing instrument, a monopolar hook, a cautery spatula, bipolar forceps, etc., and thus may include a wire attached thereto for delivery of electrical energy from a generator or a battery, for example. When such a surgical instrument 10 is used during robotic surgery, the wire often presents a challenge to the overall system architecture.

Instrument control unit 100a is configured to help manage wire(s) that extend proximally from a surgical instrument 10, for example. In particular, instrument control unit 100a includes a channel 102a extending longitudinally at least partially along an external surface of a housing 104a of the instrument control unit 100a. Channel 102a is appropriately sized to allow a wire to be removably inserted therein. Channel 102a may be made from a compliant material such as silicone, fluoroelastomer, rubber, ethylene propylene diene terpolymer ("EPDM"), nitrile rubber (e.g., Buna-N), and/or other types of elastic materials, for example. It is disclosed that the material from which the channel 102a is made has a durometer rating from between about 10 Shore A to about 100 Shore A. Additionally, the channel 102a may have an electrical resistance high enough to improve the dielectric insulation in its particular location with respect to the instrument control unit 100a.

It is further envisioned that channel 102a is made from an extrusion or a molding process. Channel 102a may also be secured between a first housing portion 104a1 and a second housing portion 104a2 of housing 104a. Additionally, it is disclosed that instrument control unit 100a includes more than one channel 102a, e.g., two parallel channels 102a, for managing more than one wire. Further, channel 102a of instrument control unit 100a may be sized and configured to releasably accept more than one wire therein. Moreover, while the cross-section of channel 102a is shown as generally U-shaped in FIG. 15, channel 102a may include other types of cross-sections such as a C-shaped cross-section, a circular cross-section including a slot, etc. Additionally, channel 102a may include radial and/or axial ribs to help frictionally retain the wire(s) therein, for instance. It is further envisioned that channel 102a can be adhered to an instrument control unit to increase the functionality of the instrument control unit. Additionally, it is envisioned that instrument drive assembly 200 includes a similar channel as channel 102a of instrument control unit 100a. Such a channel may be radially aligned with channel 102a.

Figure 16:
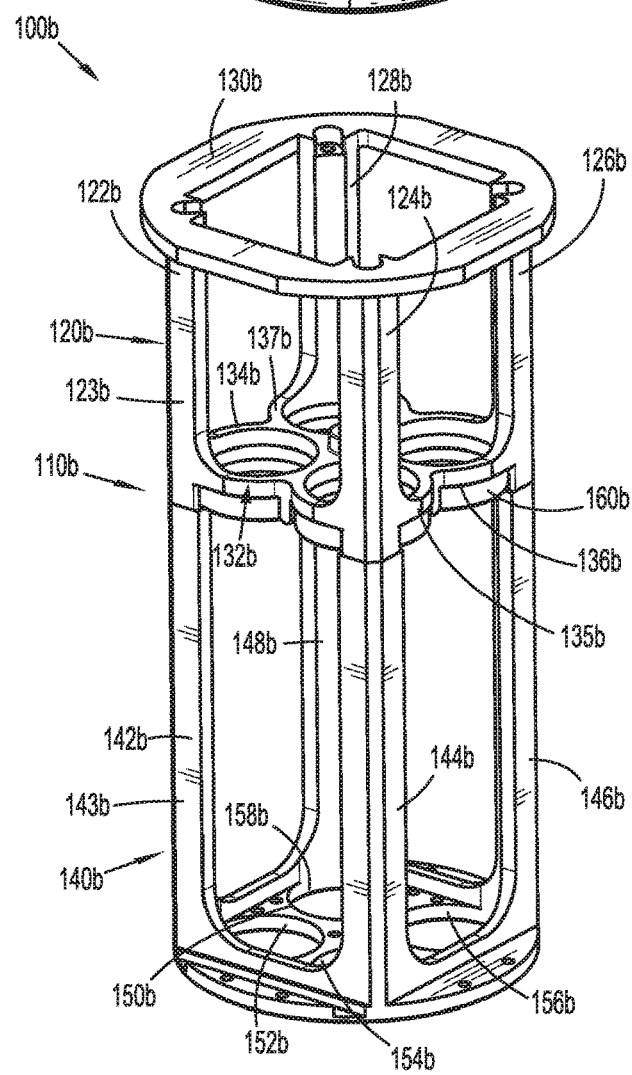
FIG. 16 is a perspective view of a frame of an instrument control unit in accordance with embodiments of the present disclosure.
Figure 17:
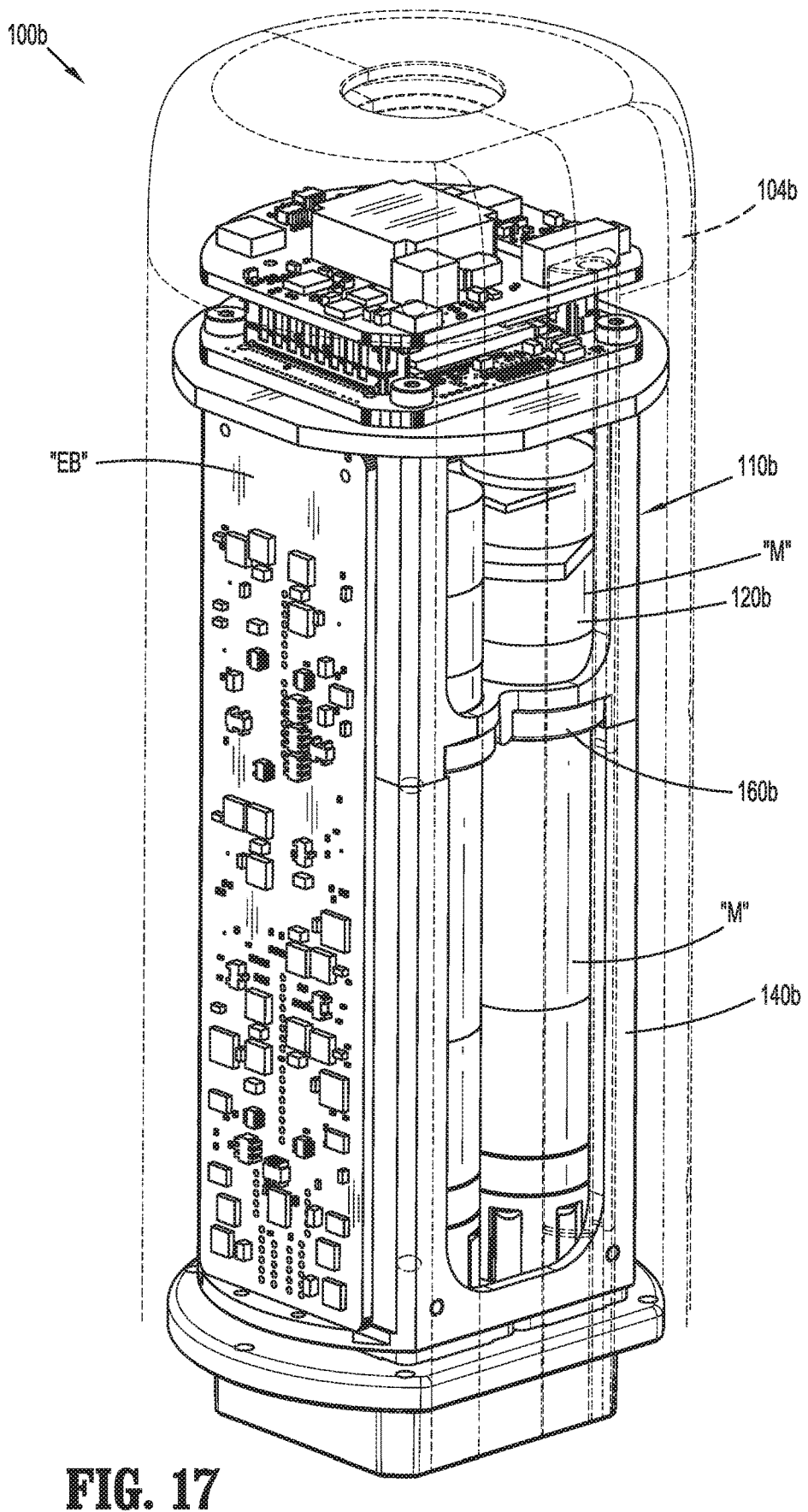
FIG. 17 is a perspective view of the instrument control unit of FIG. 16 with portions thereof shown in phantom.

Referring now to FIGS. 16 and 17, another embodiment of an instrument control unit is shown and is indicated by reference character 100b. In this embodiment, a frame 110b of instrument control unit 100b is shown. Frame 110b includes a proximal rigid structure 120b, a distal rigid structure 140b, and a compliant member 160b. Proximal rigid structure 120b and distal rigid structure 140b may be made from metal, plastic, and/or additional material(s) with a relatively high compressive strength and a relatively high torsional strength. Compliant member 160b may be made from a compliant material such as silicone, fluoroelastomer, rubber, ethylene propylene diene terpolymer ("EPDM"), nitrile rubber (e.g., Buna-N), and/or other types of elastic materials, for example.

Proximal rigid structure 120b includes a first corner post 122b, a second corner post 124b, a third corner post 126b, a fourth corner post 128b, a proximal ring 130b, and a distal motor mount 132b. Each corner post 122b, 124b, 126b and 128b includes an L-shaped cross-section. Additionally, mounting surfaces 123b are defined on external-facing surfaces of the corner posts 122b, 124b, 126b and 128b (FIG. 16). Distal motor mount 132b includes four rings 134b, 135b, 136b and 137b, each for engaging a motor "M" (FIG. 17).

Distal rigid structure 140b includes a first corner post 142b, a second corner post 144b, a third corner post 146b, a fourth corner post 148b, and a distal motor mount 150b. Each corner post 142b, 144b, 146b and 148b includes an L-shaped cross-section. Additionally, mounting surfaces 143b are defined on external-facing surfaces of the corner posts 142b, 144b, 146b and 148b (FIG. 16). Distal motor mount 150b includes four rings 152b, 154b, 156b and 158b, each for engaging a motor "M" (FIG. 17) of instrument control unit 100b.

It is envisioned that proximal rigid structure 120b and distal rigid structure 140b are disposed in a telescoping relationship with one another. It is further envisioned that proximal rigid structure 120b and distal rigid structure 140b are assembled together and form a single rigid structure.

Proximal rigid structure 120b and distal rigid structure 140b provide the framework for assembly of the instrument control unit 100b, enable electrical boards "EB," sensors and connectors to be reliably mounted thereto (e.g., mounting surfaces 143a, 143b), provide a conductive, thermal mass to help control and mitigate heat (e.g., via conduction and convection) generated from electronics and/or motors "M." Additionally, proximal rigid structure 120b and distal rigid structure 140b may be used as an electrically conductive frame to help with grounding and shielding electricity. Further, proximal rigid structure 120b and distal rigid structure 140b help isolate and protect sensitive components therewithin, and facilitate assembly and serviceability due to the ability of an instrument housing 104b to be assembled onto and/or removed from proximal rigid structure 120b and distal rigid structure 140b without interfering with the functionality of instrument control unit 100b.

Compliant member 160b is disposed in contact with a distal portion of distal motor mount 132b of proximal rigid structure 120b, and is configured for contact with motors "M." The inclusion of compliant member 160b (which may be omitted from instrument control unit 100b) helps ensure the motors "M" remain rigidly in position during intended and unintended use (e.g., when instrument control unit 100b bumps into another piece of equipment or a person, for example), as compliant member 160b acts as a cushion. Further, due to its compliance and elasticity, compliant member 160b helps reduce manufacturing tolerances between adjacent components and thus lowers manufacturing costs and creates a more robust instrument control unit 100b.

It is envisioned that compliant member 160b is any suitable shape and thickness. For example, compliant member 160b may be four ring-shaped members that are joined at adjacent outer edges. Such a ring-shaped compliant member 160b may be helpful for mounting portions or motors "M." Additionally, instrument control unit 100b may include more than one compliant member 160b. For instance, a second compliant member 160b may be disposed proximally of distal motor mount 150b.

Referring now to FIGS. 18-21, an embodiment of instrument drive assembly is shown and is indicated by reference character 200a. Instrument drive assembly 200a includes a housing assembly 205a including a proximal housing 210a and a distal housing 220a. As discussed below, instrument drive assembly 200a includes a locking mechanism including various features to help enable and/or facilitate a robust, one-handed, and/or secure connection between proximal housing 210a and distal housing 220a.

Figure 18:
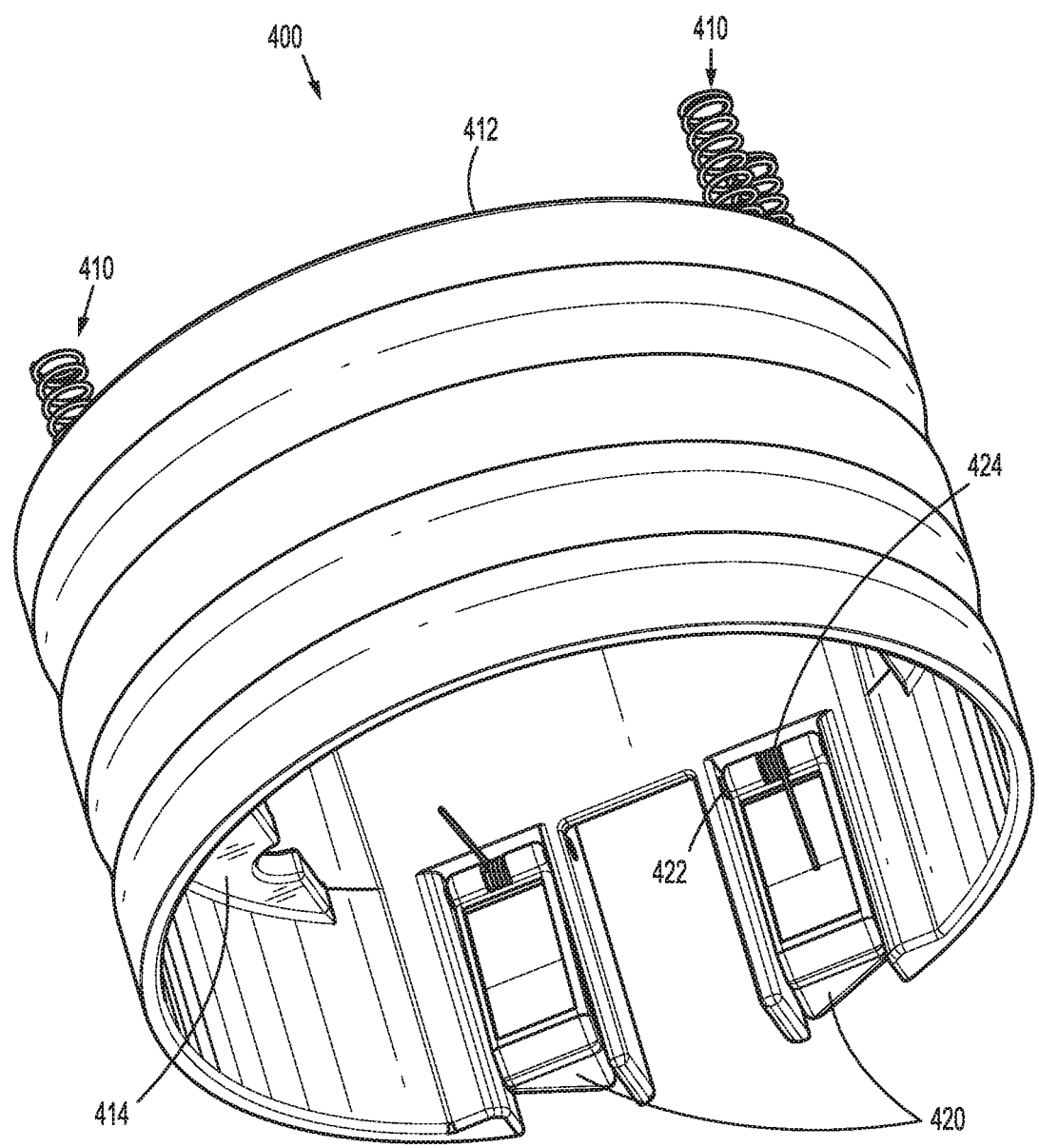
FIG. 18 is a perspective view of a locking collar of an instrument control unit in accordance with embodiments of the present disclosure.

Proximal housing 210a includes a locking collar 400 that is configured to mechanically engage a flexure ring 450 of proximal housing 210a. With particular reference to FIG. 18, locking collar 400 is hollow, cylindrically shaped, and includes a plurality of biasing members 410, and a plurality of pawls 420. The biasing members 410 are disposed on a proximal portion or a proximal face 412 of locking collar 400. In disclosed embodiments, each biasing member 410 is a compression spring. Further, each biasing member 410 is configured to contact a portion of proximal housing 210a to urge locking collar 400 distally.

In the embodiment illustrated in FIG. 18, two pawls 420 are shown. Each pawl 420 is rotatable about a pin 422, and is urged radially inwardly by a biasing element, e.g., a torsion spring 424.

Figure 19:
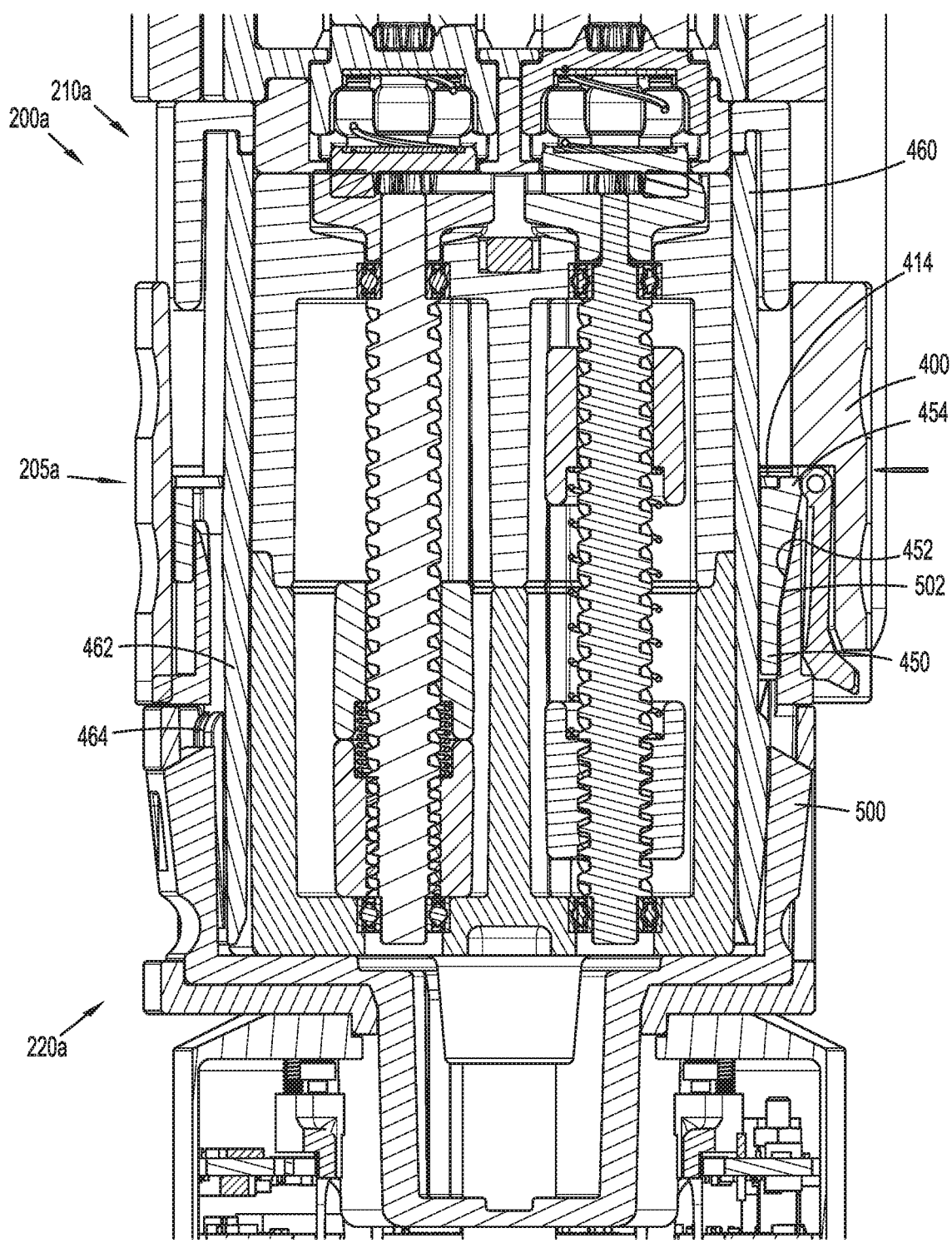
FIG. 19 is a cross-sectional view of the instrument control unit including the locking collar of FIG. 18.
Figure 19A:
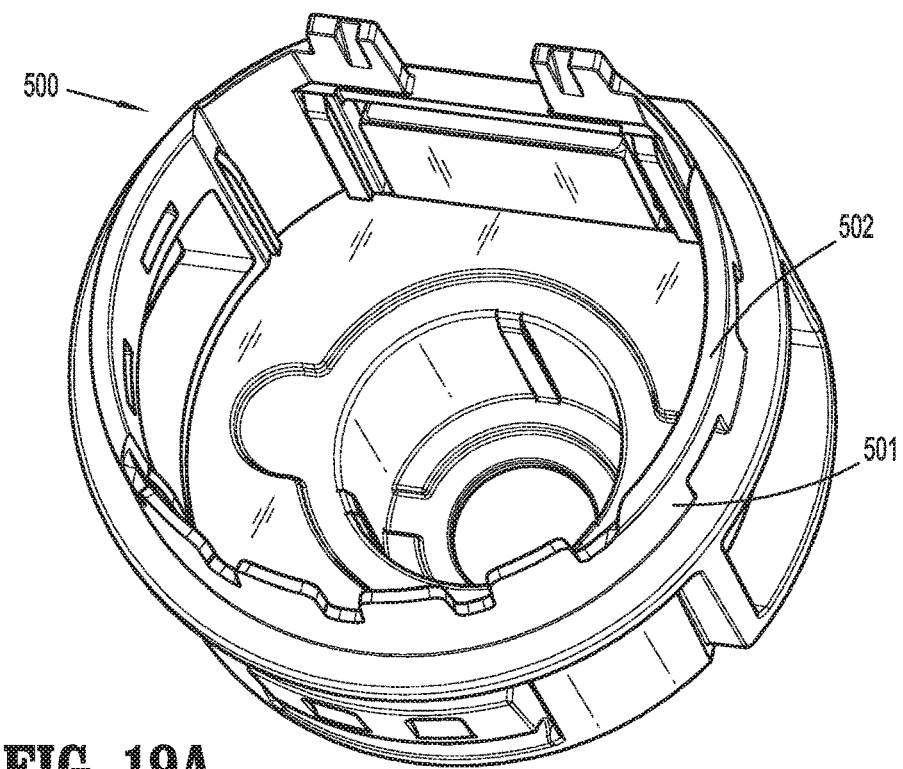
FIG. 19A is a perspective view of a cup of the instrument control unit of FIG. 19.
Figure 19B:
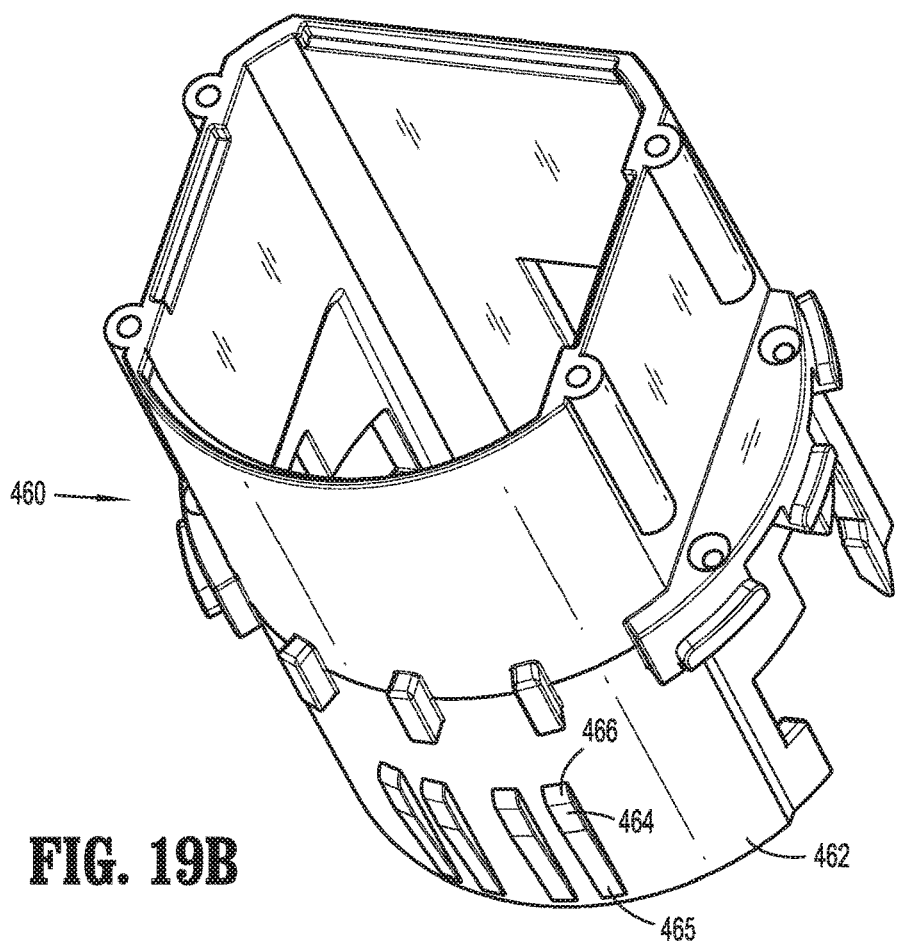
FIG. 19B is a perspective view of a locking ring of the instrument control unit of FIGS. 19 and 19A.
Figure 20:
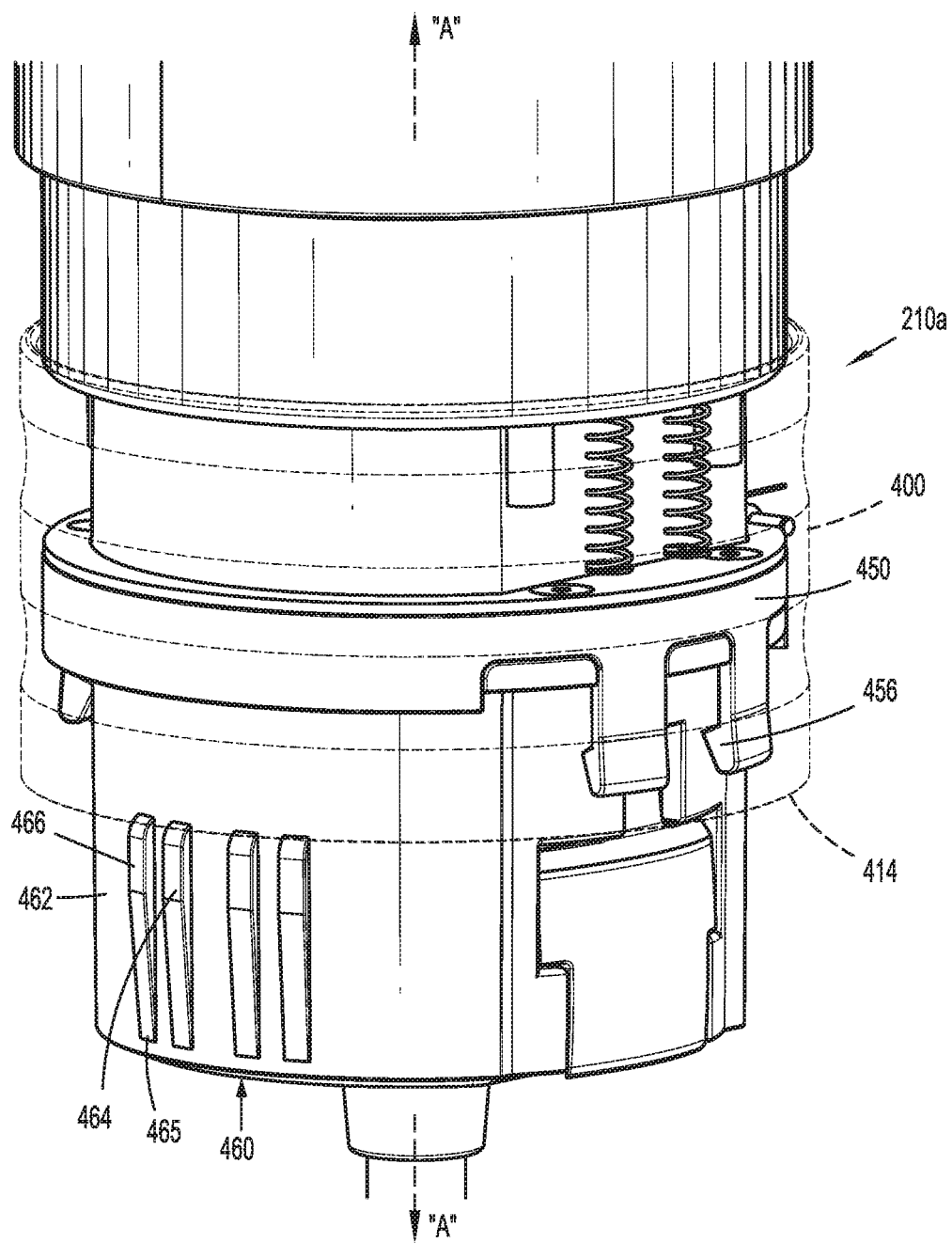
FIGS. 20 and 21 are perspective views of portions of the instrument control unit of FIGS. 18 and 19.
Figure 21:
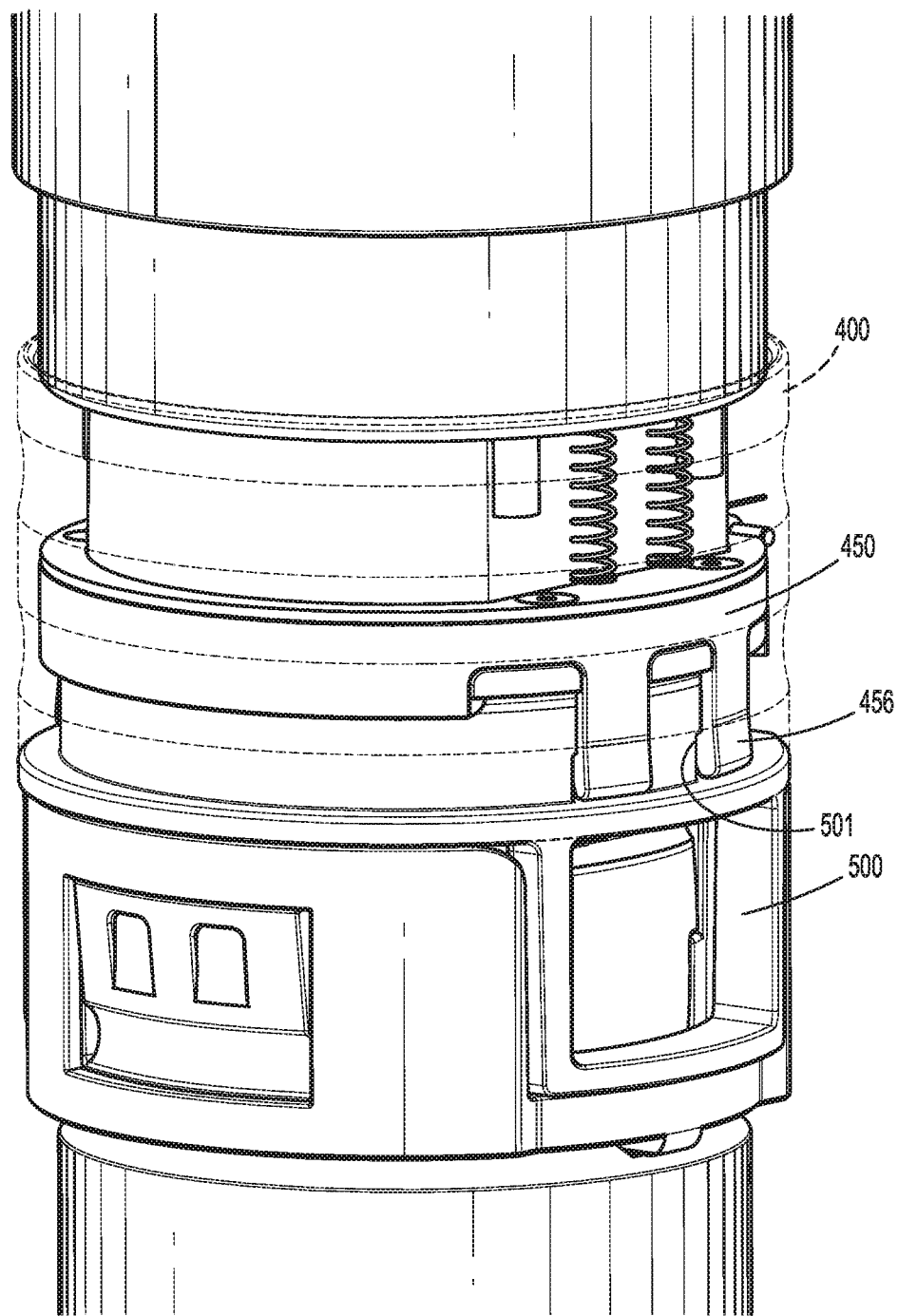

With reference to FIGS. 19-21 a flexure ring 450 of proximal housing 210a is shown. Flexure ring 450 is ring-like and is positioned radially outwardly of a locking ring 460. Flexure ring 450 includes a tapered portion 452 configured to engage a corresponding tapered portion 502 of a cup 500 of the distal housing 220a. With particular regard to FIGS. 19, 19A and 19B, the engagement between the tapered portion 452 of the flexure ring 450 and the tapered portion 502 of the cup 500 prevents distal movement of the flexure ring 450 with respect to the cup 500, and thus prevents distal movement of the proximal housing 210a with respect to the distal housing 220a. Fingers 456 of flexure ring 450 are biased radially outwardly and are configured to engage a lip 501 of cup 500 (see FIG. 21) when locking collar 400 is in its distal location.

Pawls 420 help ensure that fingers 456 of flexure ring 450 are locked in place before locking ring 460 locks into place. Tapered portion 502 of cup 500 kicks pawls 420 out of position to enable locking as the instrument drive unit 200c advances towards the robot arm 2, 3.

Further, the biasing members 410 of the locking collar 400 urge the locking collar 400 distally such that a distal engagement surface 414 of the locking collar 400 exerts a distal force on a proximal engagement surface 454 of the flexure ring 450, which thus helps prevent axial movement of the proximal housing 210a with respect to the distal housing 220a (see FIG. 19). Accordingly, when the locking collar 400 is moved a predetermined distance proximally against the bias of biasing members 410, fingers 456 of flexure ring 450 flex radially outwardly thus allowing axial movement between proximal housing 210a and distal housing 220a.

Referring now to FIGS. 19, 19A, 19B and 20, locking ring 460 is shown. Locking ring 460 is part of the proximal housing 210a and is disposed radially inwardly of flexure ring 450 and cup 500, and portions of locking ring 460 are in direct contact with flexure ring 450 and cup 500. Locking ring 460 includes a body 462, and a plurality of spaced-apart protrusions 464 extending radially outward from a distal portion of the body 462 (FIG. 20). Each protrusion 464 is longitudinally tapered such that a distal-most portion 465 of the protrusion 464 is closer to the longitudinal axis "A-A" than a proximal portion 466 of the protrusion 464. The protrusions 464 (or crush ribs) are configured to engage corresponding cavities (not explicitly shown) within cup 500 of distal housing 220a. Accordingly, when the locking ring 460 is engaged with the cup 500, radial or rotational movement between the proximal housing 210a (including locking ring 460) and the distal housing 220a (including cup 500) is minimized or eliminated.

With continued reference to FIGS. 18-21, the engagement and disengagement between proximal housing 210a and distal housing 220a of instrument drive assembly 200a is described. To engage proximal housing 210a and distal housing 220a, distal housing 220a is moved toward proximal housing 210a until lip 501 of cup 500 is moved proximally past fingers 456 of flexure ring 450, thus causing fingers 456 to flex radially outward and into engagement with lip 501. To disengage or remove distal housing 220a from proximal housing 210a, a user moves the locking collar 400 a predetermined distance proximally against the bias of biasing members 410, such that fingers 456 of flexure ring 450 flex radially outwardly out of engagement with lip 501 of cup 500. In this position, distal housing 220a is movable distally with respect to proximal housing 210a, and out of engagement with proximal housing 210a.

Referring now to FIGS. 22-26, an interface 600 between instrument control unit 100 and instrument drive assembly 200 is shown. Interface 600 is configured to transfer movement from driving elements (e.g., gear motors, brushless DC electric motors, brushed motors, stepper motors, servomotors, piezo drive motors, internal combustion drives, pneumatic- and hydraulically-powered drives, etc.) within instrument control unit 100 to driven elements (e.g., surgical instruments) engaged with instrument drive assembly 200. Additionally, interface 600 maintains sterility between instrument control unit 100 and instrument drive assembly 200, provides a location for mounting sensors and for electrical connections, for example.

Generally, interface 600 includes a proximal body portion 610, a distal body portion 620, a plurality of proximal couplers 640, and a plurality of distal couplers 650. A proximal portion 641 of each proximal coupler of the plurality of proximal couplers 640 extends through an opening 612 of proximal body portion 610, and a distal portion 651 of each distal coupler of the plurality of distal couplers 650 extends through an opening 622 of distal body portion 620. Additionally, each proximal coupler 640 is mechanically engaged with a corresponding distal coupler 650, as described in further detail below (see FIGS. 24 and 25). It is envisioned that proximal body portion 610 and distal body portion 620 are connectable to each other (e.g., selectively connectable and disconnectable) with suitable elements, such as screws or other mechanical fasteners. Such connectability enables to a user to perform maintenance and/or replace components of interface 600.

Proximal couplers 640 are configured for engagement with driving elements of instrument control unit 100, and distal couplers are configured for engagement with driven elements of instrument drive assembly 200. Further, interface 600 is configured such that rotation of the plurality of proximal couplers 640 via the driving elements of the instrument control unit 100 results in a corresponding rotation of the plurality of distal couplers 650, and thus corresponding rotation of the driven elements of the instrument drive assembly 200.

Figure 26:
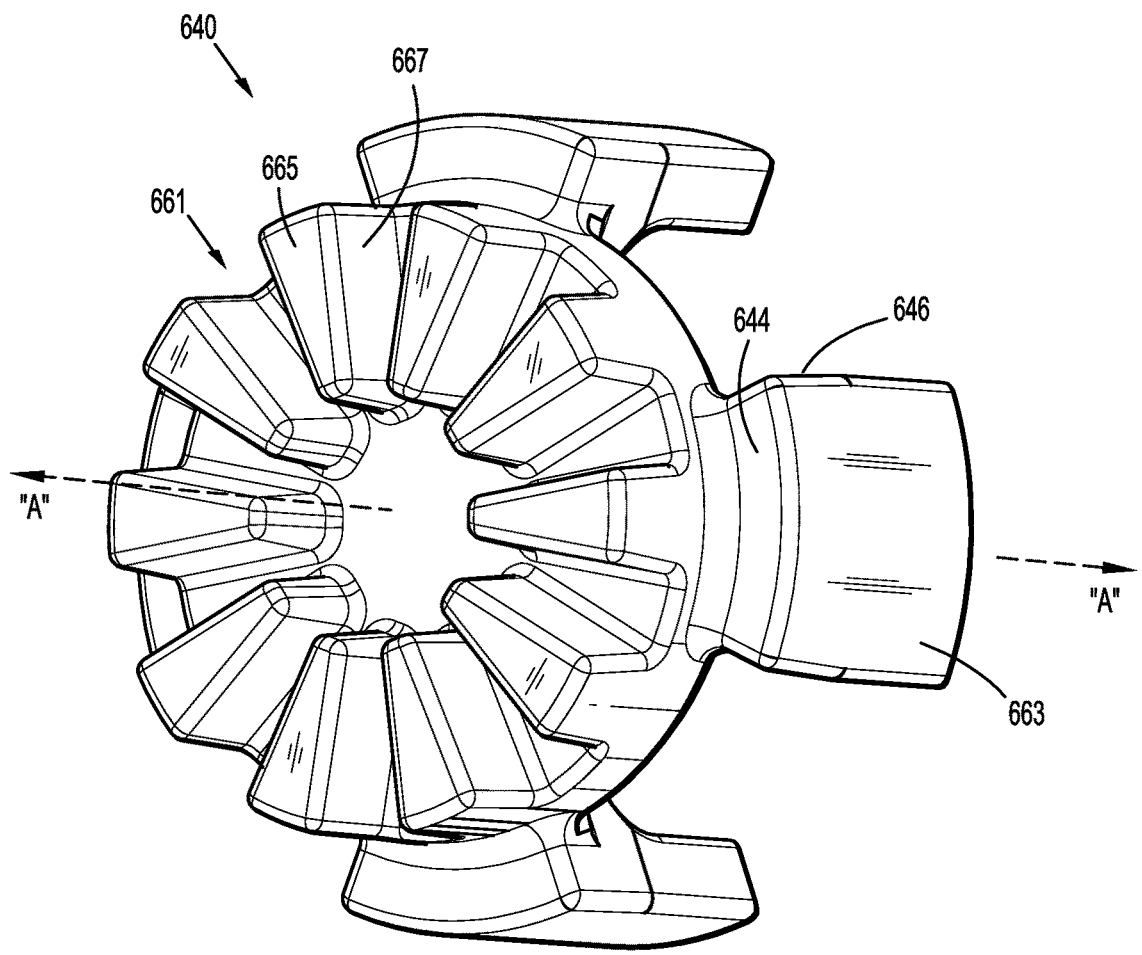
FIG. 26 is a perspective view of a coupler of the interface of FIGS. 22-25.

With reference to FIG. 26, a single coupler of plurality of couplers 640 is shown. In disclosed embodiments, proximal coupler 640 and distal coupler 650 are substantially the same as each other with the exception of an outer diameter of proximal coupler 640 is different (e.g., smaller) than an outer diameter of distal coupler 650 (see FIG. 24, for example). Coupler 640 includes a mating surface 661 and a plurality of legs 663. The mating surface 661 is configured to engage a driving element of instrument control unit 100 or a driven element of the instrument drive assembly 200. That is, the mating surface of proximal coupler 640 is configured to engage a driving element of instrument control unit 100, and the mating surface of distal coupler 650 is configured to engage a driven element of the instrument drive assembly 200. More particularly, mating surface 661 includes a plurality of spaced-apart protrusions 665, which each include a pair of tapered surfaces 667 (i.e., longitudinal tapered with respect to the longitudinal axis "A-A"; see FIG. 24). The tapered surfaces 667 help increase the necessary tolerances, and thus lower the cost and increase the robustness of the system.

Plurality of legs 663 of coupler 640 includes four legs 663 radially spaced about coupler 640. In use, legs 663 of proximal coupler 640 inter-engage and are in contact with legs 654 of distal coupler 650. More particularly, proximal coupler 640 and distal coupler 650 are 45° out of phase with one other, resulting in each leg 663 from proximal coupler 640 being between and in contact with two legs 654 from distal coupler 650. Similarly, each leg 654 from distal coupler 650 is between and in contact with two legs 663 from proximal coupler 640. Accordingly, rotation of legs 663 of proximal coupler 640 causes a corresponding rotation of legs 654 of distal coupler 650.

Figure 24:
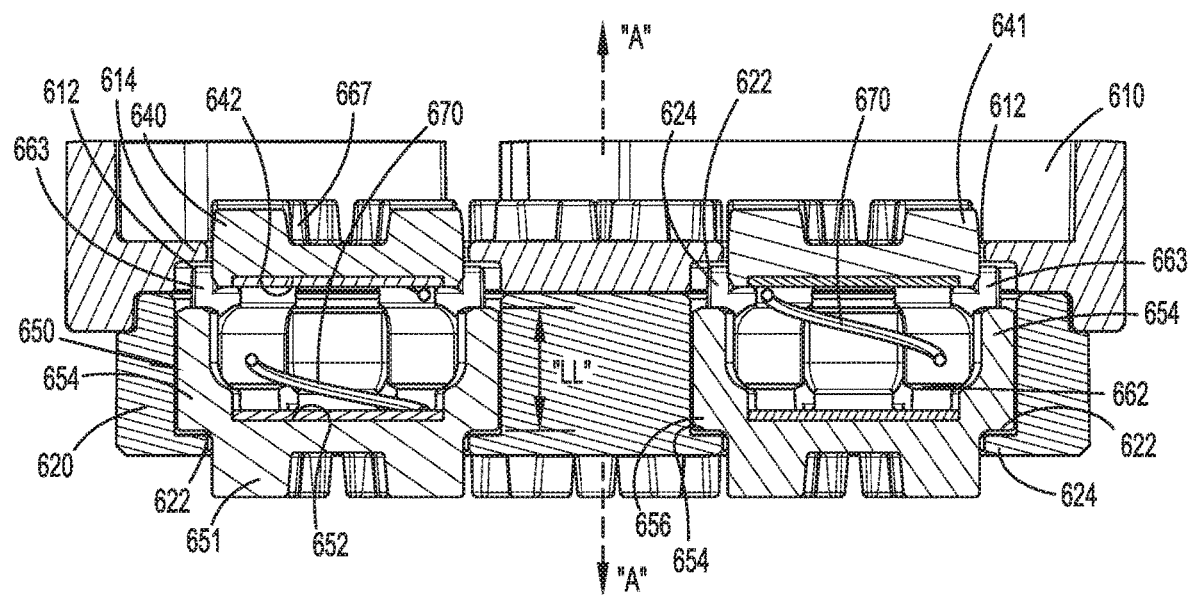
FIGS. 24 and 25 are cross-sectional views of the interface of FIGS. 22 and 23 in accordance with embodiments of the present disclosure.

Further, the longitudinal length "LL" of legs 663 and legs 654 is longer than half of the longitudinal length of a cavity 662 defined between proximal coupler 640 and distal coupler 650, thus resulting in longitudinal overlap between legs 663 of proximal coupler 640 and legs 654 of distal coupler 650 (see FIG. 24). These overlapping surfaces reduce stack height and help prevent moving surfacing from engaging stationary surfaces.

In use, rotation of a driving element of instrument control unit 100 causes a corresponding rotation of proximal coupler 640, rotation of proximal coupler 640 and its legs 644 causes rotation of distal coupler 650, which results in rotation of a driven element of instrument drive assembly 200.

A first embodiment of interface 600 is shown in FIG. 24. Here, a biasing element 670 (e.g., a compression spring) is disposed within cavity 662 between corresponding proximal couplers 640 and distal couplers 650. The force provided by biasing element 670 can be selected for a particular purpose.

Each biasing element 670 is in contact with a distal face 642 of proximal coupler 640 and a proximal face 652 of distal coupler 650, thereby proximally biasing proximal coupler 640 and distally biasing distal coupler 650. Further, a distal face 612 of a lip 614 of proximal body portion 610 limits the proximal movement of proximal coupler 640 by engaging a proximal surface 644 of a step 646 of proximal coupler 640. Additionally, a proximal face 625 of a lip 624 of distal body portion 620 limits the distal movement of distal coupler 650 by engaging a distal surface 657 of a step 656 of distal coupler 650.

Figure 25:
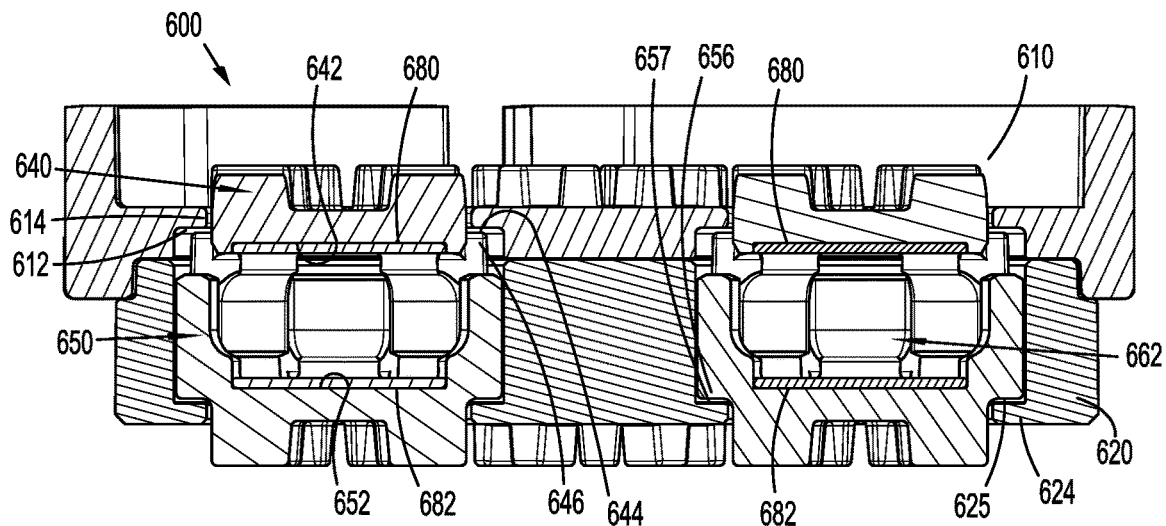

A second embodiment of interface 600 is shown in FIG. 25. Here, a first magnet 680 is disposed within cavity 662 and in mechanical engagement with proximal coupler 640, and a second magnet 682 is disposed within cavity 662 and in mechanical engagement with distal coupler 650. More particularly, each first magnet 680 is in contact with distal face 642 a corresponding proximal coupler 640, and each second magnet 682 is in contact with a proximal face 652 of a corresponding distal coupler 650. Additionally, first magnet 680 may be longitudinally or axially fixed with regard to proximal coupler 640, and second magnet 682 may be longitudinally or axially fixed with regard to distal coupler 650.

The strength, orientation and polarities of first magnets 680 and second magnets 682 are such that each first magnet 680 longitudinally or axially repels the corresponding second magnet 682, such that the magnets 680, 682 are biased away from each other. The force provided by the magnets 680, 682 can be selected for a particular purpose. Further, distal face 612 of lip 614 of proximal body portion 610 limits the proximal movement of proximal coupler 640 by engaging proximal surface 644 of step 646 of proximal coupler 640. Additionally, proximal face 622 of lip 624 of distal body portion 620 limits the distal movement of distal coupler 650 by engaging distal surface 654 of step 656 of distal coupler 650.

It is further envisioned that a sensor (e.g., a hall sensor) is included within cavity 662 or in connection with at least one magnet (e.g., each of the first magnets 680 and each of the second magnets 682) to help constantly track the position (e.g., rotational position) of associated proximal couplers 640 and/or distal couplers 650 (e.g., for system monitoring).

Figure 1C:
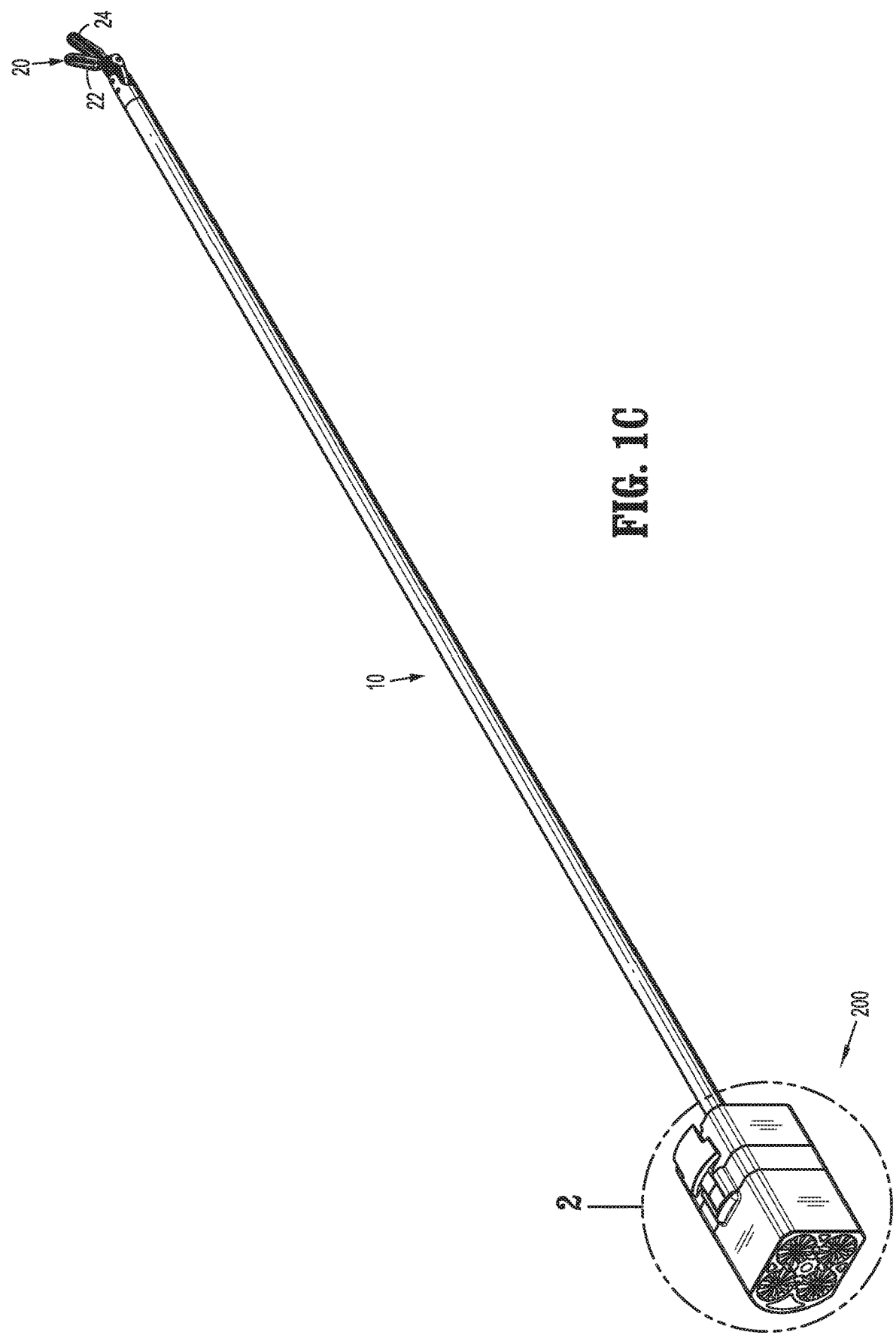
FIG. 1C is a perspective view of an instrument drive assembly in accordance with embodiments of the present disclosure.
Figure 27:
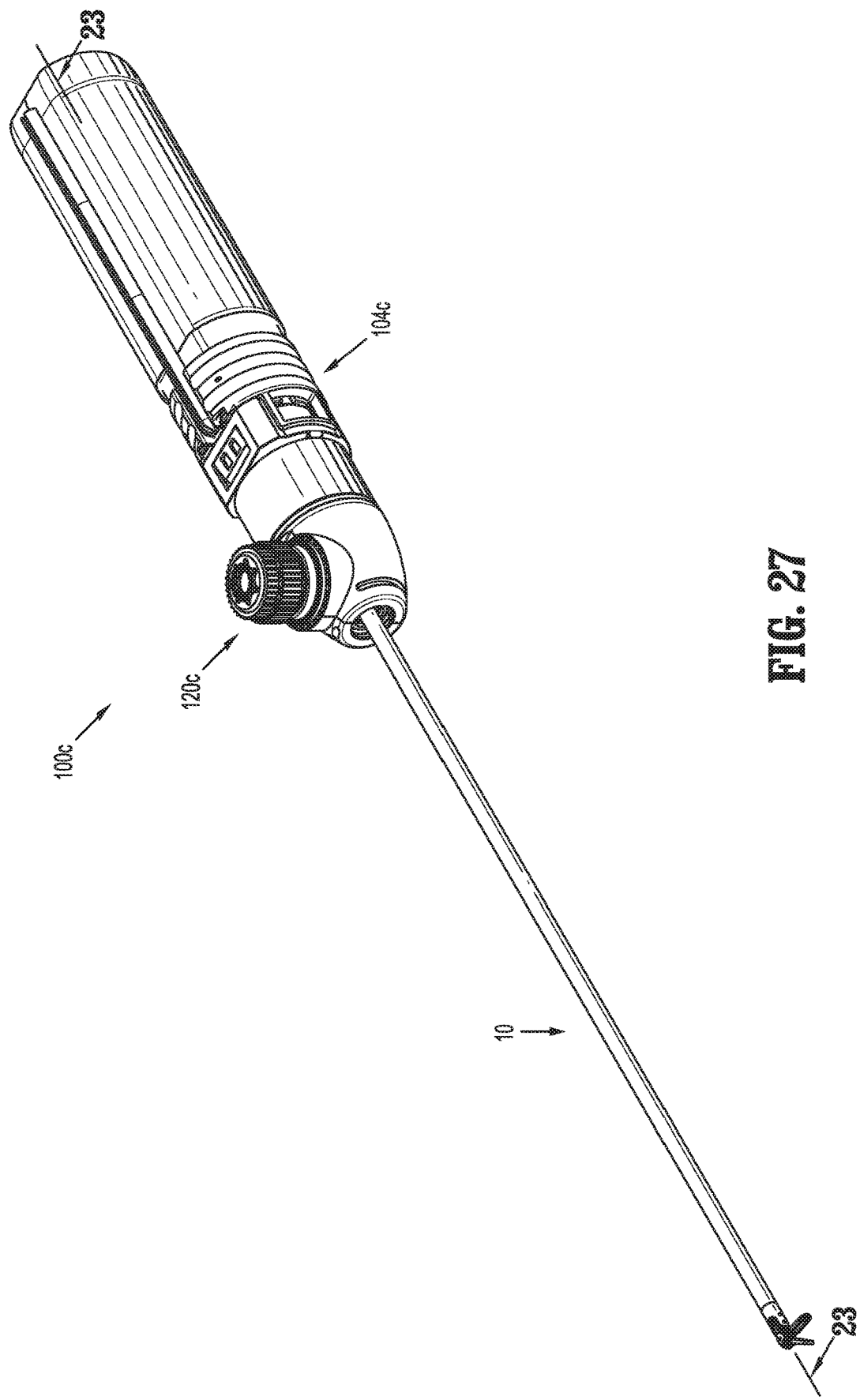
FIGS. 27 and 28 are perspective views of an instrument control unit in accordance with embodiments of the present disclosure, illustrated with a surgical instrument attached thereto.
Figure 28:
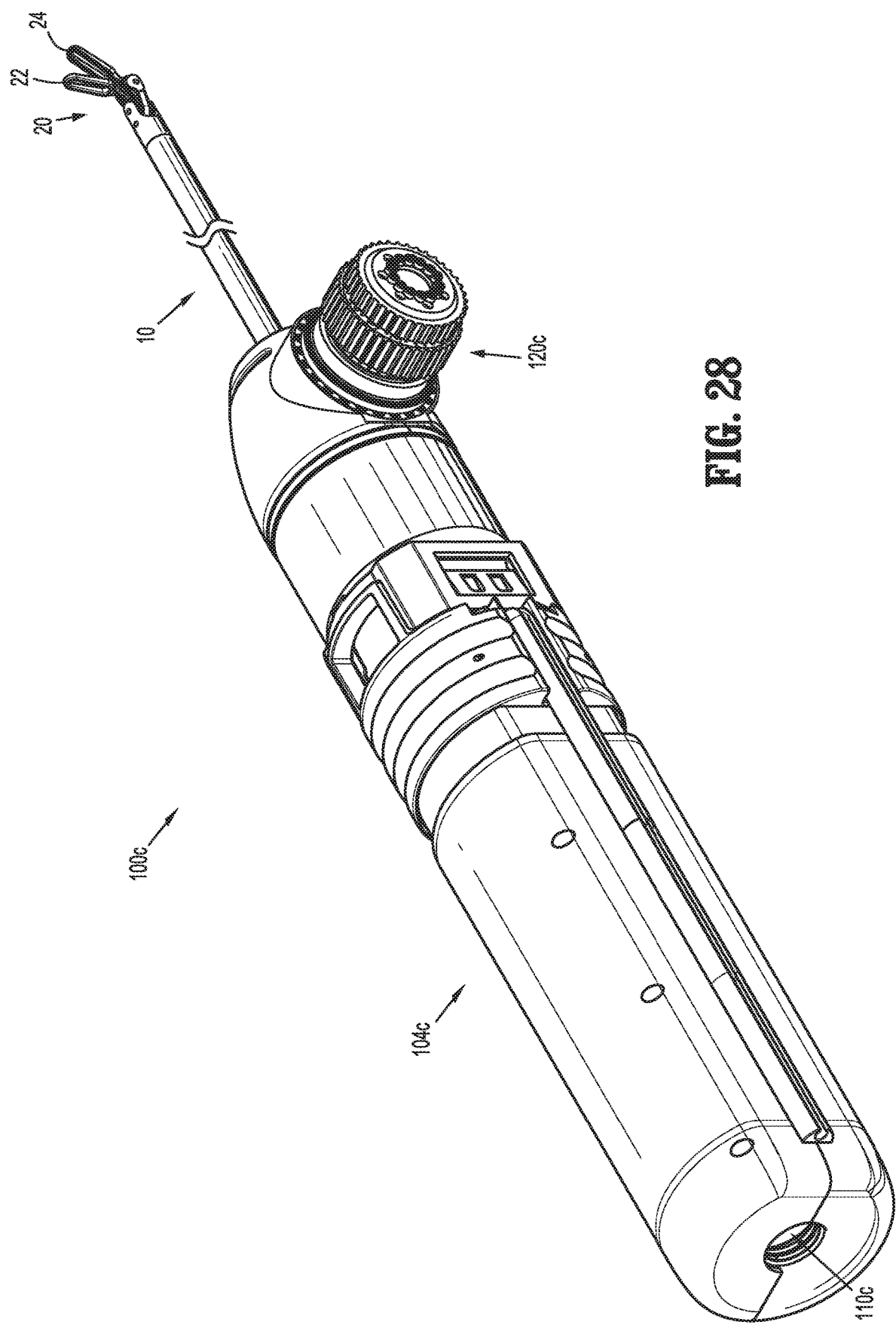
Figure 29:
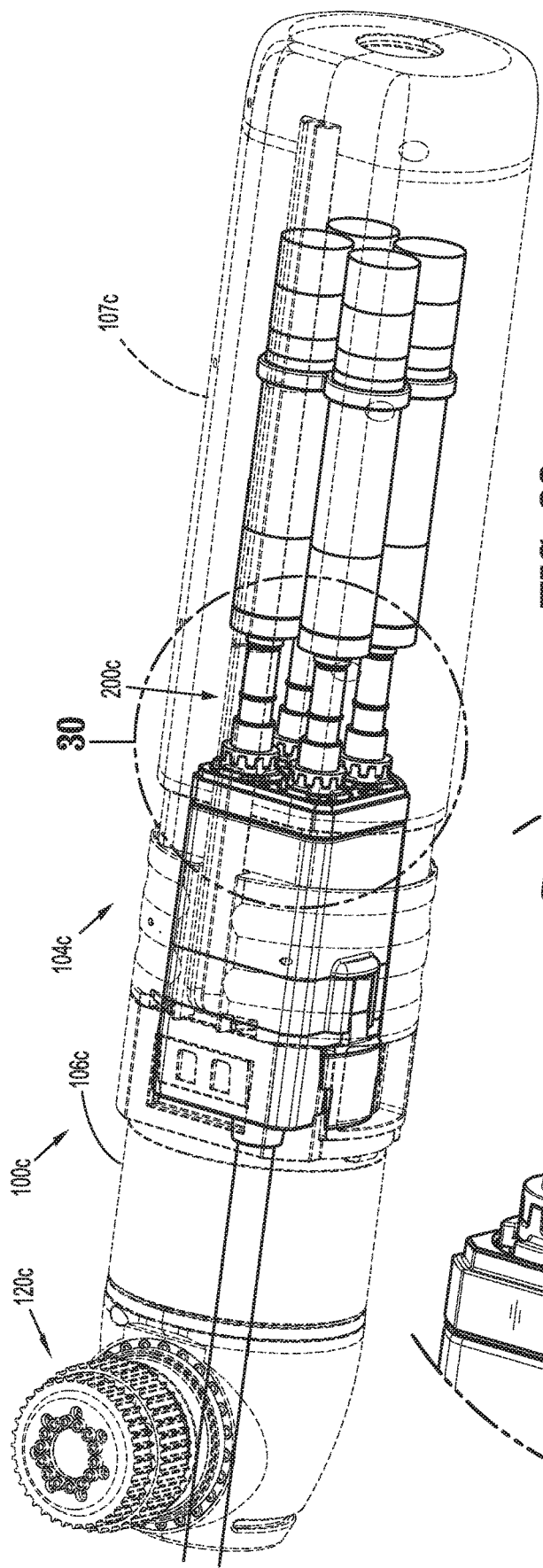
FIG. 29 is a perspective view of the instrument control unit of FIGS. 27 and 28.
Figure 30:
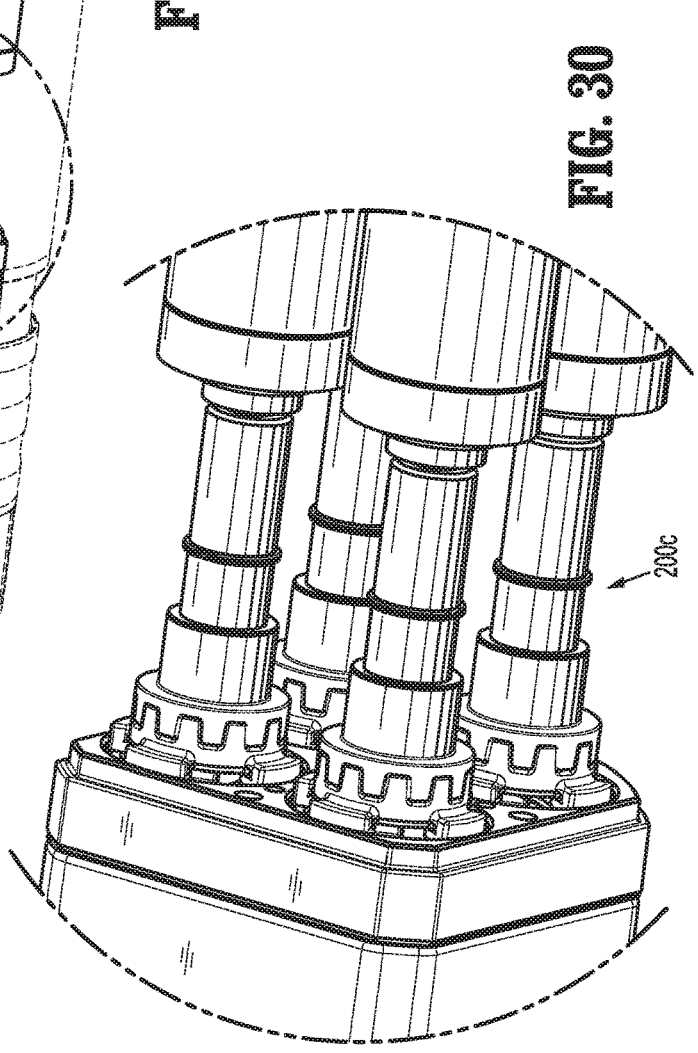
FIG. 30 is an enlarged view of the area of detail indicated in FIG. 29.
Figure 31:
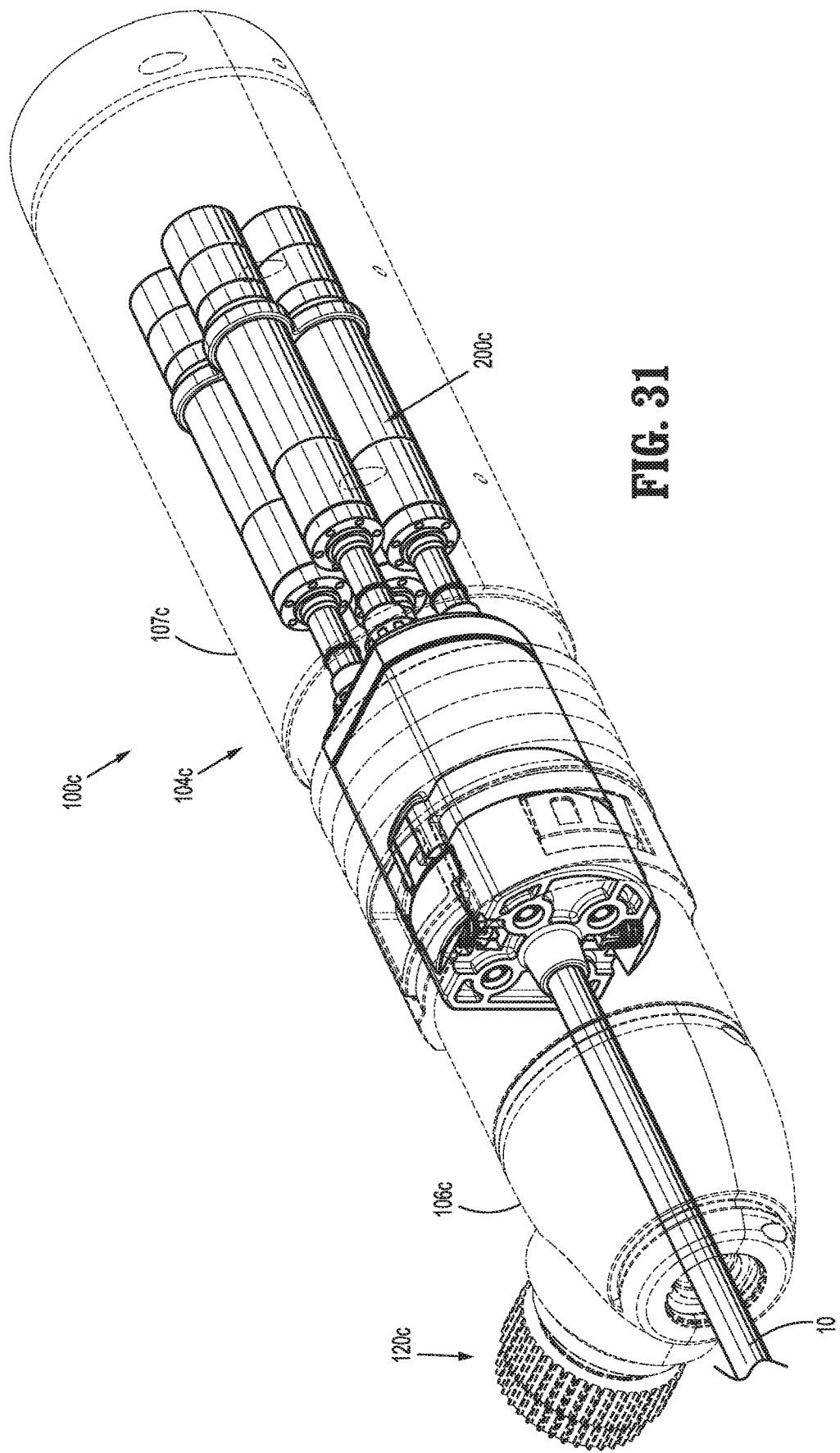
FIG. 31 is a perspective view of the instrument control unit of FIGS. 27-30 illustrated with a surgical instrument attached thereto.
Figure 32:
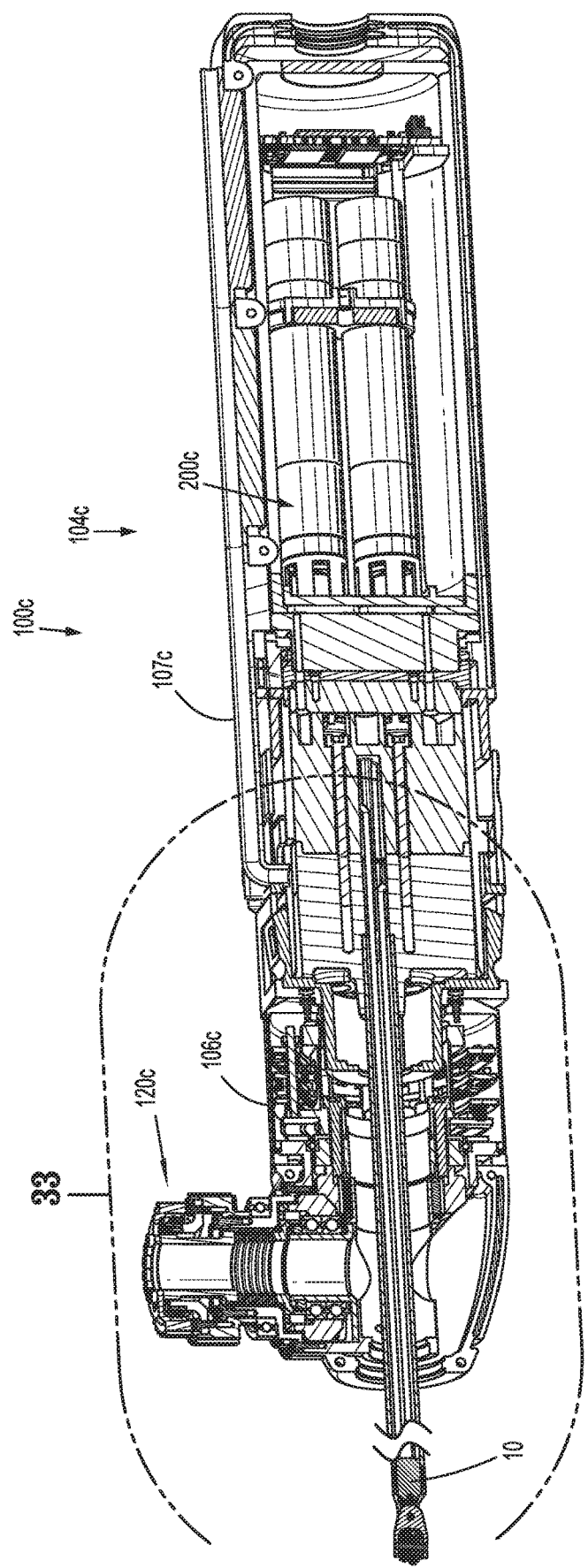
FIG. 32 is a cut-away view of the instrument control unit of FIGS. 27-31.

Referring now to FIGS. 27-33, another embodiment of an instrument control unit is shown and is indicated by reference character 100c. Instrument control unit 100c includes a housing 104c including an instrument drive unit 200c connected thereto. Instrument drive unit 200c may be similar in operation and function to instrument drive unit 200 discussed above, or other instrument drive units. Additionally, FIGS. 27 and 28 illustrate surgical instrument 10 (as shown in FIG. 1C, for example) extending at least partially through a cavity or tube 110c defined within housing 104c. Tube 110c of housing 104c defines a longitudinal axis "B-B." While the illustrated surgical instrument 10 is shown supporting end effector 20 having jaw members 22 and 24, any reasonable type of surgical instrument can be used in connection with instrument control unit 100c.

Figure 33:
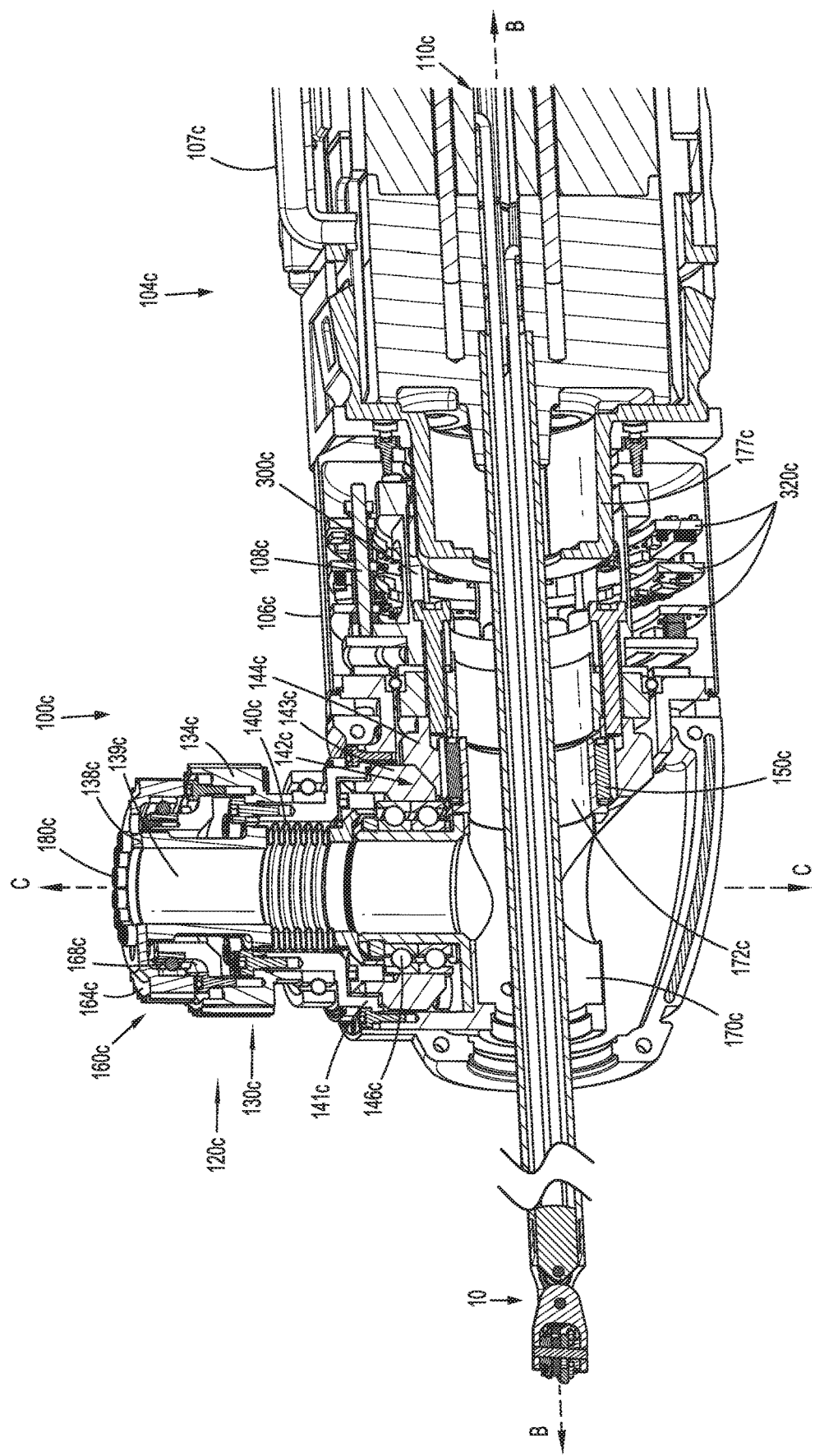
FIG. 33 is an enlarged view of the area of detail indicated in FIG. 32.

Housing 104c of instrument control unit 100c includes a lateral port 120c configured for mechanical engagement with one robot arm 2, 3 (see FIG. 1A). As shown in FIG. 33, lateral port 120c defines an axis "C-C," which is perpendicular or substantially perpendicular to longitudinal axis "B-B" of tube 110c. Lateral port 120c includes a first drive assembly 130c configured to facilitate rotation of a portion of housing 104c about longitudinal axis "B-B," and a second drive assembly 160c configured to facilitate rotation of lateral port 120c about axis "C-C."

Figure 22:
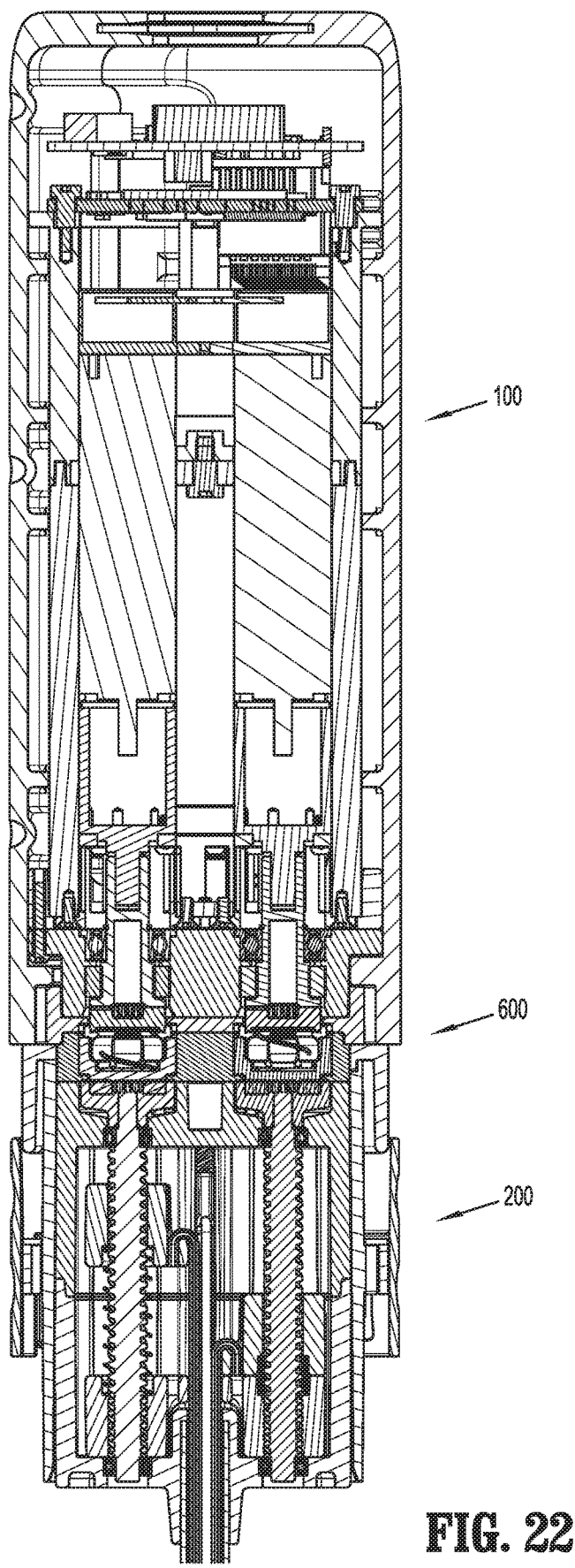
FIG. 22 is a cross-sectional view of an instrument control unit including an interface in accordance with embodiments of the present disclosure.
Figure 23:
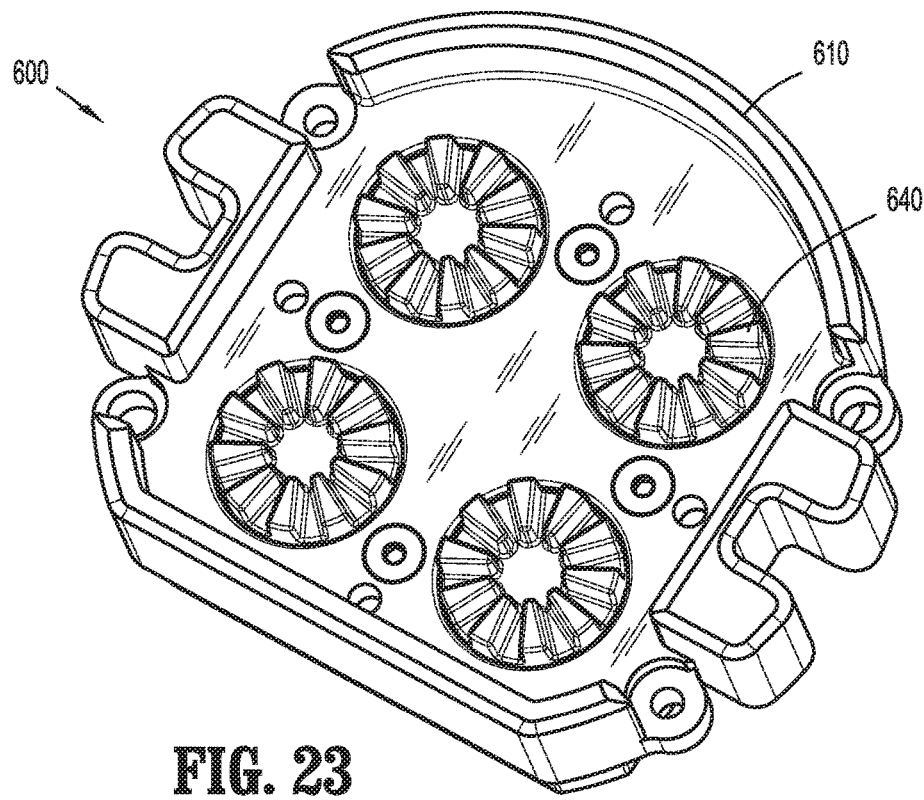
FIG. 23 is a perspective view of the interface of FIG. 22.

With continued reference to FIG. 33, a distal portion 106c of housing 104c of instrument control unit 100c is rotatable about longitudinal axis "B-B." Additionally, lateral port 120c is rotatable about longitudinal axis "B-B." More particularly, distal portion 106c of housing 104c is rotatable with respect to a proximal portion 107c of housing 104c; lateral port 102c is rotatable with respect to proximal portion 107c of housing 104c. That is, actuation of first drive assembly 130c of lateral port 120c causes both distal portion 106c of housing 104c and lateral port 120c to rotate about longitudinal axis "B-B" with respect to proximal portion 107c of housing 104c. As shown in FIGS. 20, 22 and 23, instrument drive unit 200c is housed within proximal portion 107c of housing 104c.

With particular reference to FIG. 33, first drive assembly 130a includes a first drive gear 134c, a drive shaft 138c, a bevel gear set 142c, a plurality of ball bearings 146c, and a roller bearing 150c. First drive gear 134c is disposed about an outer periphery of lateral port 120c, and is located laterally inward (i.e., closer to longitudinal axis "B-B") of a second drive gear 164c of second drive assembly 160c. First drive gear 134c is engagable via a gear (or other suitable structure) located on robot arm 2, 3, for example.

First drive gear 134c is mechanically coupled to drive shaft 138c, such that rotation of first drive gear 134c causes a corresponding rotation of drive shaft 138c about axis "C-C." Drive shaft 138c includes a hollow body 139c that is flexible in the direction of axis "C-C." This flexibility of drive shaft 138c is enabled by a wave spring 140c. Wave spring 140c helps ensure stiffness or rigidity of the joint, and the hollow-ness of wave spring 140c allows wires (e.g., an electrical cable) to pass through. Drive shaft 138c also includes a lip 141c extending radially outward from body 139c.

A first bevel gear 143c of bevel gear set 142c is mechanically engaged (e.g., fixedly engaged) with lip 141c of drive shaft 138c. Accordingly, rotation of drive shaft 138c about axis "C-C" causes a corresponding rotation of first bevel gear 143c about axis "C-C." A plurality of bearings 146c, e.g., a double row of ball bearings, disposed about a lateral portion 172c of a main body 170c facilitate the rotation of first bevel gear 143 about axis "C-C" and about lateral portion 172c of main body 170c.

With continued reference to FIG. 33, a second bevel gear 144c of bevel gearset 142c is mechanically engaged with first bevel gear 143c. More particularly, teeth of second bevel gear 144c inter-engage or mesh with teeth of first bevel gear 143c. Further, first bevel gear 143c and second bevel gear 144c are 90° offset from each other. Therefore, rotation of first bevel bear 143c about axis "C-C" causes a corresponding rotation of second bevel gear 144c about longitudinal axis "B-B," which is perpendicular from axis "C-C." A plurality of bearings 146c, e.g., a double row of ball bearings, disposed about lateral portion 172c of main body 170c facilitate the rotation of first bevel gear 143c about axis "C-C" and about lateral portion 172c of main body 170c.

Second bevel gear 144c is mechanically engaged with a frame 108c of distal portion 106c of housing 104c. Frame 108c is rotatable about longitudinal axis "B-B" with respect to proximal portion 107c of housing 104c. Accordingly, rotation of second bevel gear 144c results in distal portion 106c of housing 104c rotating about longitudinal axis "B-B" with respect to proximal portion 107c of housing 104c. Additionally, rotation of second bevel gear 144c results in rotation of lateral port 120c about longitudinal axis "B-B." Roller bearing 150c, disposed about a longitudinal portion 173c of main body 170c facilitates the rotation of second bevel gear 144c about axis "B-B" and about longitudinal portion 173c of main body 170c.

It is envisioned that the ability of lateral port 120c to rotate about the longitudinal axis "B-B" facilitates use of medical work station 1. That is, since lateral port 120c connects to robot arm 2, 3, the rotatability of lateral port 120c also enables the robot arm 2, 3 to move with respect to instrument control unit 100c, which may be helpful when enable rolling of the surgical instrument 10, for example.

As noted above, second drive assembly 160c is configured to facilitate rotation of lateral port 120c about axis "C-C." Second drive assembly 160c includes second drive gear 164c and a bearing 168c. Second drive gear 164c is disposed about an outer periphery of lateral port 120c, and is located laterally outward (i.e., farther from longitudinal axis "B-B") of first drive gear 134c of first drive assembly 130c. Second drive gear 164c is engagable via a gear (or other suitable structure) located on robot arm 2, 3, for example. Bearing 168c facilitates the rotation of second drive gear 164c about axis "C-C" with respect to first drive gear 134c.

With continued reference to FIG. 33, second drive assembly 160c also includes a plurality of connectors 180c (e.g., electrical and/or mechanical connectors). Connectors 180c are configured to engage corresponding connectors (not explicitly shown) on robot arms 2, 3 to help relay information and/or controls from control device 4 to instrument control unit 100c and vice versa, for instance.

It is envisioned that the ability of lateral port 120c to rotate about axis "C-C" facilitates use of medical work station 1. Thus, the rotatability of lateral port 120c enables the robot arm 2, 3 to move about axis "C-C" with respect to instrument control unit 100c, which may be helpful to provide pitch/yaw movement with respect to axis "B-B."

Distal portion 106c of housing 104c also includes an electro-magnetic mount 300c and a plurality of sensors 320c. Electro-magnetic mount or cavity 300c is positioned adjacent or at a proximal end of distal portion 106c of housing 104c and is configured to engage a corresponding mounting feature 177c of proximal portion 107c of housing 104c (see FIG. 33). Sensors 320c (e.g., an electronic PCBA (printed circuit board assembly) torque sensor circuit) may be ring-like and positioned adjacent a radially-outer portion of distal portion 106c of housing 104c. Sensors 320c may be configured to relay the rotational position (i.e., with respect to the longitudinal axis "B-B") of distal portion 106c with respect to proximal portion 107c of housing 104c. Additionally, electro-magnetic mount 300c may help lock or maintain the relative positions of distal portion 106c of housing 104c and proximal portion 107c of housing 104c.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An interface for use with a surgical system, the interface comprising:
a proximal body portion configured to mechanically engage an instrument control unit of the surgical system;
a distal body portion disposed in mechanical cooperation with the proximal body portion and being configured to mechanically engage an instrument drive assembly of the surgical system;
a cavity defined between the proximal body portion and the distal body portion;
a proximal coupler disposed at least partially within the cavity and being configured to engage a driving element of the instrument control unit;
a distal coupler disposed at least partially within the cavity, a distal end of the distal coupler including a distally-facing mating surface having a plurality of protrusions configured to engage a driven element of the instrument drive assembly; and
a biasing element disposed in mechanical cooperation with the proximal coupler and the distal coupler.

2. The interface according to claim 1, wherein the biasing element is configured to bias the proximal coupler proximally.

3. The interface according to claim 2, wherein the biasing element is configured to bias the distal coupler distally.

4. The interface according to claim 1, wherein the biasing element includes at least one magnet.

5. The interface according to claim 1, wherein the biasing element includes a first magnet disposed in mechanical cooperation with the proximal coupler and a second magnet disposed in mechanical cooperation with the distal coupler.

6. The interface according to claim 1, wherein the proximal coupler and the distal coupler are coaxial.

7. The interface according to claim 6, further comprising a second proximal coupler disposed at least partially within the cavity and configured to mechanically engage a second driving element of the instrument control unit, and a second distal coupler disposed at least partially within the cavity and configured to mechanically engage a second driven element of the surgical system.

8. The interface according to claim 7, wherein the second proximal coupler and the second distal coupler are coaxial.

9. The interface according to claim 1, wherein the proximal coupler includes a plurality of legs, wherein the distal coupler includes a plurality of legs, and wherein each leg of the plurality of legs of the proximal coupler is positioned adjacent two legs of the plurality of legs of the distal coupler.

10. The interface according to claim 1, wherein the proximal coupler includes a plurality of legs, wherein the distal coupler includes a plurality of legs, and wherein each leg of the plurality of legs of the proximal coupler is positioned between and in contact with two legs of the plurality of legs of the distal coupler.

* * * * *